United States Patent
Lee et al.

(10) Patent No.: US 6,287,341 B1
(45) Date of Patent: Sep. 11, 2001

(54) ORTHOPEDIC AND DENTAL CERAMIC IMPLANTS

(75) Inventors: Dosuk D. Lee, Brookline, MA (US); Christian Rey, Castanet (FR); Maria Aiolova, Brookline; Aliassghar Tofighi, Belmont, both of MA (US)

(73) Assignee: Etex Corporation, Cambridge, MA (US)

( * ) Notice: Subject to any disclaimer, the term of this patent is extended or adjusted under 35 U.S.C. 154(b) by 0 days.

(21) Appl. No.: 09/036,109

(22) Filed: Mar. 6, 1998

Related U.S. Application Data

(60) Division of application No. 08/729,343, filed on Oct. 16, 1996, which is a continuation-in-part of application No. 08/650,764, filed on May 20, 1996, now Pat. No. 6,214,368, which is a continuation-in-part of application No. 08/446,182, filed on May 19, 1995, now Pat. No. 5,676,976.

(51) Int. Cl.$^7$ ........................................... A61F 2/28
(52) U.S. Cl. ................... 623/16.11; 623/23.51; 623/23.61; 623/923; 128/888; 424/602
(58) Field of Search ............... 623/16, 66, 16.11, 623/23.51, 23.61, 523; 128/898; 424/602

(56) References Cited

U.S. PATENT DOCUMENTS

| | | |
|---|---|---|
| Re. 33,161 | 2/1990 | Brown et al. . |
| Re. 33,221 | 5/1990 | Brown et al. . |
| 4,157,378 | 6/1979 | Tomlinson et al. . |
| 4,429,691 | 2/1984 | Niwa et al. ............... 128/92 |
| 4,612,053 | 9/1986 | Brown et al. . |
| 4,684,673 | 8/1987 | Adachi . |
| 4,698,375 | 10/1987 | Dorman et al. . |
| 4,713,076 | 12/1987 | Draenert . |
| 4,722,948 | 2/1988 | Sanderson . |
| 4,737,411 | 4/1988 | Graves, Jr. et al. . |
| 4,849,193 | 7/1989 | Palmer et al. . |
| 4,880,610 | 11/1989 | Constantz . |
| 4,917,702 | 4/1990 | Scheicher et al. . |
| 4,938,938 | 7/1990 | Ewers et al. . |
| 4,959,104 | 9/1990 | Iino et al. . |
| 5,007,930 | 4/1991 | Dorman et al. ............... 623/16 |
| 5,019,379 | 5/1991 | Domb et al. ............... 424/78 |
| 5,034,059 | 7/1991 | Constantz . |
| 5,037,639 | 8/1991 | Tung . |
| 5,047,031 | 9/1991 | Constantz . |
| 5,049,157 | 9/1991 | Mittlemeier et al. ............... 623/16 |
| 5,053,212 | 10/1991 | Constantz et al. . |
| 5,085,861 | 2/1992 | Gerhart et al. . |
| 5,129,905 | 7/1992 | Constantz . |
| 5,149,368 | 9/1992 | Liu et al. . |
| 5,152,836 | 10/1992 | Hirano et al. ............... 106/690 |
| 5,164,187 | 11/1992 | Constantz et al. . |
| 5,178,845 | 1/1993 | Constantz et al. . |
| 5,262,166 | 11/1993 | Liu et al. ............... 424/423 |
| 5,264,215 | 11/1993 | Nakabayashi et al. ............... 424/423 |
| 5,279,831 | 1/1994 | Constantz et al. . |
| 5,281,265 | 1/1994 | Liu ............... 106/35 |
| 5,286,763 | 2/1994 | Gerhart et al. . |
| 5,336,264 | 8/1994 | Constantz et al. . |
| 5,342,441 | 8/1994 | Mandai et al. ............... 106/35 |
| 5,352,715 | 10/1994 | Wallace et al. ............... 523/115 |
| 5,427,754 | 6/1995 | Nagata et al. ............... 423/308 |
| 5,470,803 | 11/1995 | Bonfield et al. . |
| 5,496,399 | 3/1996 | Ison et al. . |
| 5,503,164 | * 4/1996 | Friedman ............... 128/898 |
| 5,516,532 | 5/1996 | Atala et al. ............... 424/548 |
| 5,522,893 | 6/1996 | Chow et al. . |
| 5,525,148 | 6/1996 | Chow et al. . |
| 5,542,973 | 8/1996 | Chow et al. . |
| 5,545,254 | 8/1996 | Chow et al. . |
| 5,565,502 | 10/1996 | Glimcher et al. ............... 523/115 |
| 5,605,713 | 2/1997 | Boltong . |
| 5,665,120 | 9/1997 | Ohtsuka et al. ............... 623/16 |
| 5,683,461 | * 11/1997 | Lee et al. ............... 623/16 |
| 5,691,397 | 11/1997 | Glimcher et al. ............... 523/115 |
| 5,700,289 | 12/1997 | Breitbart et al. ............... 623/16 |
| 5,782,971 | 7/1998 | Constantz et al. ............... 106/690 |

FOREIGN PATENT DOCUMENTS

| | | |
|---|---|---|
| 0268463 | 5/1988 | (EP) . |
| 0347028 | 11/1989 | (EP) . |
| 0664133 | 2/1994 | (EP) . |
| 63-111875 | 5/1988 | (JP) . |
| 63-170205 | 7/1988 | (JP) . |
| 2182261 | 7/1990 | (JP) . |
| 5305134 | 11/1993 | (JP) . |
| 06228011 | 12/1994 | (JP) . |
| 7277712 | 10/1995 | (JP) . |
| WO 92/00109 | 1/1992 | (WO) . |
| WO 92/02453 | 2/1992 | (WO) . |
| WO 94/04657 | 3/1994 | (WO) . |
| WO 94/08458 | 4/1994 | (WO) . |
| WO 94/20064 | 9/1994 | (WO) . |
| WO 95/08319 | 3/1995 | (WO) . |
| WO 94/02412 | 7/1995 | (WO) . |
| WO 96/36562 | 11/1996 | (WO) . |
| WO 97/17285 | 5/1997 | (WO) . |

OTHER PUBLICATIONS

Appel, et al., "Oncologic, Endocrine & Metabolic", Exp. Opin. Ther. Patents 4:1461, 1994.

(List continued on next page.)

*Primary Examiner*—Corrine P. McDermott
*Assistant Examiner*—Choon R. Koh
(74) *Attorney, Agent, or Firm*—Clark & Elbing, LLP

(57) ABSTRACT

A method for treating a bone defect is provided by identifying a bone site suitable for receiving an implant; and introducing a strongly resorbable, poorly crystalline apatitic calcium phosphate at the implant site, whereby bone is formed at the implant site. A bone defect may be treated by identifying a bone site suitable for receiving an implant; and introducing a hydrated precursor to a strongly resorbable, poorly crystalline apatitic calcium phosphate at the implant site, whereby the hydrated precursor is converted in vivo to a poorly crystalline apatitic calcium phosphate and whereby bone is formed at the implant site. The implant site may be a variety of sites, such as a tooth socket, non-union bone, bone prosthesis, an osteoporatic bone, an intervertebral space, an alveolar ridge or a bone fracture.

27 Claims, 24 Drawing Sheets

OTHER PUBLICATIONS

Blumenthal, et al., "Effect of Preparation Conditions on the Properties and Transformation of Amorphous Calcium Phosphate", Mat. Res. Bull 7(11):1181 (Nov. 1972).

Butterman, et al. "The Use of Bone Allografts in the Spine", Clinical Orthopaedics and Related Research, 342:75, 1996.

Cowley, "Protheses for Primary Total Hip Replacement", International Journal of Technology Assessment in Health Care, 11:(4):770 1995.

Driessens,et al. "Calcium Phosphate Bone Cements", Encyclopedia Handbook of Biomaterials and Bioengineering, 855–877, 1995.

Fukase, et al. "Setting Reactions and Compressive Strengths of Calcium Phosphate Cements", J. Dent. Res. 69(12):1852, Dec., 1990.

Hardwick, et al., "Devices for Dentoalveolar Regeneration: An Up–to–Date Literature Review", J. Periodontol, 66(6):495 (Jun., 1995).

Hollinger, et al., "Role of Bone Substitutes", Clinical Orthopaedics and Related Research, 324:55, 1996.

Horioglu, et al., Long Term Follow–up of Hydroxyapatte Cement (HAC) Implants for Craniofacial Reconstruction, 21st Meeting of Society for Biomaterials, Mar. 18–22, 1995, San Francisco, CA.

Misch, et al., "The Repair of Localized Severe Ridge Defects for Implant Placement Using Mandibular Bone Grafts", Implant Dent, 4(4):261 (1995).

Misch, et al., "Bone–Grafting Materials in Implant Denistry", Implant Dent, 2(3):158 (1993).

Shindo, et al., "Facial Skeletal Augmentation Using Hydroxyapatite Cement", Arch Otolaryngol Head Neck Surg—vol. 119, Feb., 1993.

Abboudi et al., "Development of Organic and Polymer Carriers for Demineralized Bone Matrix: Effect on Bone Cell Behavior," Fifth World Biomaterials Congress, May 29–Jun. 2, 1996, Toronto, Canada.

Aoki, "Science and medical applications of hydroxyapatite", JAAS, pp. 11–15, 1991.

Attawia et al., "The Long Term Osteoblast Response to Poly(anhydrise–co–imides): A New Degradable Polymer for Use in Bone," Fifth World Biomaterials Congress, May 29–Jun. 2, 1996, Toronto, Canada.

Barton et al., "Surface and bulk properties of amorphous calcium phoaphate" Colloid Interface Sci. [Proc. Int. Conf], 50th 3:71 [CA 87:73954v] (Abstract).

Besic et al., "Electron probe microanalysis of noncarious enamel and dentin and calcified tissues in mottled teeth", J. Dent. res., 48:131, (1969).

Constantz et al., "Skeletal repair by in situ formation of the mineral phase of bone", Science, 267: 1976 (1995).

Ducheyne et al., "Bioceramic Composites", Chapter 15 from An Introduction to Bioceramics, Advanced Series in ceramics, vol. 1.

Eanes et al., "Intermediate states in the precipitation of hydroxyapatite", Nature, 208: 365–367 (1965).

Eanes et al., "Intermediate phases in the basic solution preparation of alkaline earth phosphates" Calcified Tissue Res., 2(1):38 (1968) [CA 69:110373f] (Abstract).

Eanes, "Thermochemical studies on amorphous calcium phsophate", Calc. Tiss. Res., 5:133, (1970).

Fenner et al., "High Strength Partially Absorbable Composites Produced by Sintering Method for Internal Bone Fixation," Fifth World Biomaterials Congress, May 29–Jun. 2, 1996, Toronto, Canada.

Gao, T.J. "Established competence of Bioactive Composite Bone Substitute on the Healing of Diaphyseal Segmental Defects in Sheep," Fifth World Biomaterials Congress, May 29–Jun. 2, 1996, Toronto, Canada.

Glimcher et al., "Recent studies of the mineral phase in bone and its possible linkage to the organic matrix by protein-bound phosphate bonds", Phil. Trans. R. Soc. Lond., B 304:479–508, 1984.

Glimcher et al., "Recent Studies of Bone Minerals: Is the Amorphous Calcium Phosphate Theory Valid?" J. Crystal Growth, 53: 100–119 (1981).

Graves et al., "Resorbable Ceramic Implants", J. Biomed. Mater. Res. Symposium, No. 2 (Part 1), pp. 91–115 (1971).

Greenfield et al., "Formation chemistry of amorphous calcium phosphates prepared from carbonate containing solutions", Calc. Tiss. Res., 9:152 (1972).

Hirasawa et al., "Manufacture of high purity hydroxyapatite," Chemical Abstracts, 108 (10), p. 166, No. 78193h (Mar. 7, 1988).

Holmes et al., "Surface areas by gas adsorption on amorphous calcium phosphate and crystalline hydroxyapatite", Calc. Tiss. Res., 7:163 (1971).

Ishikawa et al., "Effects of preparation in aqueous solution on properties of hydroxyapatites", Dent. Mater. J. 9(1):58 (1990) [CA 113:218168j] (Abstract).

Jones et al., "Poly [L–Lactide] and Poly [L–Lactide] Ceramic Filled Composites: A Long Term in vivo/in vitro Degradation Study," Fifth World Biomaterials Congress, May 29–Jun. 2, 1996, Toronto, Canada.

Kamei et al., "Implantation of hydroxyapatite–bonded polymer," Fifth World Biomaterials Congress, May 29–Jun. 2, 1996, Toronto, Canada.

Kim et al., "Hyaluronan Based Biodegradable Scaffolds for Skeletal Tissue Reconstruction," Fifth World Biomaterials Congress, May 29–Jun. 2, 1996, Toronto, Canada.

Kinoshita et al., "Reconstruction of Mandibular Discontinuity Defects in Dogs using Autogenic Particulate Cancellous Bone and Marrow and Poly(L–lactide) mesh," Fifth World Biomaterials Congress, May 29–Jun. 2, 1996, Toronto, Canada.

Labarthe et al., "Sur la structure et les properiétés des aparities carbonatées de type B phospho–calciques", Ann. Chem., 8:289 (1973).

Ladizesky et al., "Hydrostatic Extrusion of Hydroxyapatite Polyethylene Composite", Fifth World Biomaterials Congress, May 29–Jun. 2, 1996, Toronto, Canada.

Liu et al., "Nano–Apatite/Polymer Composites II, Surface Modification of Nano–Apatite by Grafting of Polyehtylene Glycol," Fifth World Biomaterials Congress, May 29–Jun. 2, 1996, Toronto, Canada.

Nylen et al., "Molecular and ultrastructural studies of non-crystalline calcium phosphates", Calc. Tiss. Res., 9:95 (1972).

oka et al., "Development of Artificial Osteo–Chondral Composite Material," Fifth World Biomaterials Congress, May 29–Jun. 2, 1996, Toronto, Canada.

Otsuka et al., "Effect of particle size of metastable calcium phosphates on mechanical strength of a novel self–setting bioactive calcium phosphate", J. Biomed. Mat. Res., 29:25 (1995).

Pool, "Coral chemistry leads to human bone repair", Science, 269:1772 (Mar. 1995).

Posner et al., "Synthetic amorphous calcium phsophate and its relation to bone mineral structure", Bone Mineral Structure, 8:273–281 (1975).

Rey et al., "The carbonate environment in bone mineral: a resolution–enhanced fourier transform infrared spectroscopy study", Calcif. Tissue Int., 45:157 (1989).

Rey et al., "Structural studies of the mineral phase of calcifying cartilage", J. Bone Min. Res., 6:515 (1991).

Rey et al., "Preparation of Microporous Ceramic at Low Temperature from Poorly Crystalline Apatite", Symposium Abstract, 1993.

Rizkalla et al., "Effect of Composition on Strength of Bioactive Composites," Fifth World Biomaterials Congress, May 29–Jun. 2, 1996, Toronto, Canada.

Saifullin, R.S., "Physical Chemistry of Inorganic Polymeric and Composite Materials", Chapter 1: Introduction, Ellis Horwood, New York.

Selmani et al., "Biorodible Polyester Foams for Orthopaedic Tissue Culture," Fifth World Biomaterials Congress, May 29–Jun. 2, 1996, Toronto, Canada.

Ternine et al., "Amorphous/Crystalline Interrelationships in Bone Material", Calc. Tiss. Res. 1, 8–23 (1967).

Törmälä, P., "Biodegradable Self–Reinforced Composite Materials; Manufacturing Structure and Mechanical Properties", Clinical Materials 10:29–34 (1992).

Tung et al., "An intermediate state in hydrolysis of amorphous calcium phosphate", Calcif. Tissue Int., 35:783 (1983).

Slone, et al., "Fixation Techniques and Instrumentation Used in the Cervical Spine", Imaging Orthoped, Hardware, 33(2):213 (Mar., 1995).

Yasue, et al., "Effect of Adsorption of Succinic Acid on the Formation of Amorphous Calcium Phosphate", Journal of the Ceramic Society of Japan (Japanese Version), 102(12):1122, 1994.

Anthanasou et al., "Current Concepts Review: Cellular Biology of Bone–Resorbing Cells", J. Bone and Joint Surg., 78–A:1096–1112, 1996.

Hayes et al., "Augmentation of Cementless Femoral Stems to Improve Initial Stability Using a Remodelable Calcium–Phosphate Bone Material Substitute", $61^{st}$ Annual American Academy of Orthopedic Surgeons Meeting, New Orleans, Feb., 1994.

Norian Corporation, The Material Science of Norian SRS, Skeletal Repair System.

Rey, et al., "Chemical Properties of Poorly Crystalline Apatites" Phosphorous Res. Bull, 6:67–70 (1996), Abstract Only.

* cited by examiner

ORTHOPEDIC AND DENTAL CERAMIC IMPLANTS

This application is a divisional application of co-pending application U.S. Ser. No. 08/729,343, filed Oct. 16, 1996, which is a continuation-in-part application of application U.S. Ser. No. 08/650,764 filed May 20, 1996, now U.S. Pat. No. 6,214,368, entitled "Novel Bone Substitution Material and a Method of Its Manufacture", which is a continuation-in-part application of application U.S. Ser. No. 08/446,182 filed May 19, 1995 U.S. Pat. No. 5,676,976 entitled "Synthesis of Reactive Amorphous Calcium Phosphates", each of which are hereby incorporated in its entirety by reference. This application also is related to several co-pending applications filed on Oct. 16, 1996: U.S. Ser .No. 08/729,344, entitled, "Method and Products Related to the Physical Conversion of Reactive Amorphous Calcium Phosphate", U.S. Ser. No. 08/729,342, entitled, "Delivery Vehicle", U.S. Ser. No. 08/729,354, entitled, "Cell Seeding of Ceramic Compositions" and U.S. Ser. No. 08/732,016, U.S. Pat. No. 6,026,742, entitled, "Bioresorbable Ceramic Composites", each of which is incorporated by reference.

FIELD OF THE INVENTION

This invention relates to orthopedic and dental implants containing a poorly-crystalline apatitic calcium phosphate and their use as a bone graft material.

BACKGROUND OF THE INVENTION

Calcium phosphates are the principal constituent of hard tissues (bone, cartilage, tooth enamel and dentine). Naturally-occurring bone mineral is made of nanometer-sized, poorly-crystalline calcium phosphate with an apatitic structure. The poorly crystalline apatitic calcium phosphate of bone is distinguished from the more crystalline hydroxyapatites and non-stoichiometric hydroxyapatites by its distinctive x-ray diffraction pattern as shown in FIG. 1. Unlike the ideal stoichiometric crystalline hydroxyapatite, $Ca_{10}(PO_4)_6(OH)_2$, with atomic Ca/P ratio of 1.67, the composition of bone mineral is significantly different and may be represented by the following formulae,

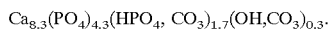

$$Ca_{8.3}(PO_4)_{4.3}(HPO_4, CO_3)_{1.7}(OH, CO_3)_{0.3}.$$

Bone mineral non-stoichiometry is primarily due to the presence of divalent ions, such as $CO_3^{2-}$ and $HPO_4^{2-}$, which are substituted for the trivalent $PO_4^{3-}$ ions. Substitution by $HPO_4^{2-}$ and $CO_3^{2-}$ ions produces a change of the Ca/P ratio, resulting in Ca/P ratio which may vary between 1.50 to 1.70, depending on the age and bony site. Generally, the Ca/P ratio increases during aging of bone, suggesting that the amount of carbonate species typically increases for older bones. It is the Ca/P ratio in conjunction with nanocrystalline size and the poorly-crystalline nature that yields specific solubility property of the bone minerals. And because bone tissues undergo constant tissue repair regulated by the mineral-resorbing cells (osteoclasts) and mineral-producing cells (osteoblasts), solubility behavior of minerals is important in maintaining a delicate metabolic balance between these cell activities.

Synthetic bone graft material made to closely resemble natural bone minerals can be a useful replacement for natural bone. Acceptable synthetic bone can avoid the problem of availability and harvesting of autologous bone (patient's own bone) and the risks and complications associated with allograft bone (bone from a cadaver), such as risks of viral transmission. An ideal synthetic bone graft should possess a minimum of the following four properties: (1) it should be chemically biocompatible; (2) it should provide some degree of structural integrity in order to keep the graft in place and intact until the patient's own bone heals around it; (3) it should be resorbable so that the patient's own bone ultimately replaces the graft; and, (4) because it may be necessary to incorporate cells and/or biomolecules into the synthetic bone material, it is desirable that the process used to form the material employ low temperatures and chemically mild conditions. Similar criteria are also important for other hard tissue grafts (e.g. cartilage).

These criteria may be met by a material in which parameters, such as Ca/P ratios, crystal size, crystallinity, porosity, density, thermal stability and material purity are controlled. While there have been considerable attempts to synthesize a ceramic material which closely resembles natural bone for use as implants, synthetic hydroxyapatite has traditionally been the preferred choice. Previous bone ceramics often involved stoichiometric apatites with significant crystalline form often with larger crystal sizes. The prior art (LeGeros R. Z., in *Calcium Phosphates in Oral Biology and Medicine*, Karger Pub. Co., New York, 1991) teaches that highly crystalline form of hydroxyapatite is produced by solution precipitation followed by sintering at high temperatures (800–1200° C.). High temperature treatment yields highly stoichiometric hydroxyapatite with crystal sizes on the order of several microns with Ca/P of 1.67. Such highly crystalline hydroxyapatite has an extremely low solubility rendering it essentially insoluble in the host tissue. Therefore, it is not replaced by living bone tissue and it remains intact in the patient for an extended period.

A bone growth implant should possess sufficient mechanical strength to support the bone. But it is preferably bio-erodible so that the bone will eventually support its own weight. This is a problem with metal pins which are commonly used to bind a fracture together. Although the pins possess sufficient mechanical strength to support the bone as it heals, this strength never diminishes and the bone never strengthens to a point that is it able to bear its body weight. The development of a material which would provide the requisite mechanical strength and a satisfactory bioerosion rate is desired.

A number of calcium phosphate bone fillers and cements have been referred to as "bioresorbable." Generally, these are compounds comprising or derived from tricalcium phosphate, tetracalcium phosphate or hydroxyapatite. These materials all have significantly greater crystalline character than the poorly crystalline apatitic calcium phosphate found in bone. At best these materials may be considered only "weakly" resorbable. Of these, the tricalcium phosphate compounds have been demonstrated to be the most resorbable and after many years of study they are still not widely used in clinical settings. The tricalcium phosphates are known to have lengthy and somewhat unpredictable resorption profiles, generally requiring in excess of one year for resorption. Furthermore, unless steps are taken to produce extremely porous or channeled samples, the tricalcium phosphates are not replaced by bone. Recently it has been concluded that the "biodegradation of TCP, which is higher than that of Hap [hydroxyapatite] is not sufficient" (Berger et al., Biomaterials, 16:1241 (1995)). Tetracalcium phosphate and hydroxyapatite derived compounds are also only weakly resorbable. Tetracalcium phosphate fillers generally exhibit partial resorption over long periods of time such as 80% resorption after 30 months (Horioglu et al., Soc. for Biomaterials, March 18–22, pg 198 (1995)).

There remains a need for a synthetic bone material that more closely mimics the properties of naturally occurring minerals in bone. In particular, there remains a need to provide synthetic bioceramics which are completely bioresorbable and biocompatible. The use of such a resorbable calcium phosphate in biomedical devices provides many advantages over alternative conventional materials. For instance, it eliminates the need for post-therapy surgery to remove the device and degrades in the human body to biocompatible, bioresorbable products.

SUMMARY OF THE INVENTION

The present invention provides a ceramic implant device using a poorly crystalline apatitic calcium phosphate that is biocompatible, bioresorbable and highly reossifying, which may be used in orthopedic and dental applications as a bone substitute material. The ceramic material may be formed at low temperatures, is readily formable and/or injectable, and yet can harden to high strength upon further reaction, making it well-suited for implantation. The ceramic composite material contains a poorly crystalline apatitic calcium phosphate with Ca/P ratios comparable to naturally occurring bone minerals. The ceramic material is strongly bioresorbable and its mechanical properties can be adjusted to meet the demands of the particular therapy and/or implant site and/or to biodegrade at a specified rate. The material may be used as a filler in bone defects, as a bone cement, and in bone plates, bone screws and other fixtures and medical devices. Implants are suitable for use in both humans and animals.

The material of the invention may be obtained by converting an amorphous calcium phosphate in the presence of a limited quantity of water to produce a hydrated precursor into a poorly crystalline apatitic calcium phosphate. The conversion is associated with hardening of the paste and produces a poorly crystalline apatitic calcium phosphate.

According to one aspect of the invention, a bone defect is treated by identifying a bone site suitable for receiving an implant; and introducing a strongly resorbable, poorly crystalline apatitic calcium phosphate at the implant site, whereby bone is formed at the implant site.

According to another aspect of the invention, a bone defect may be treated by identifying a bone site suitable for receiving an implant; and introducing a hydrated precursor to a strongly resorbable, poorly crystalline apatitic calcium phosphate at the implant site, whereby the hydrated precursor is converted in vivo to a poorly crystalline apatitic calcium phosphate and whereby bone is formed at the implant site.

In preferred embodiments, the hydrated precursor is introduced as a paste or a putty to the implant site. The implant site may include tooth socket, alveolar ridge, non-union bone, bone prosthesis, osteoporotic bone, intervertabral space, cranial defect, cartilaginous site, or a bone fracture site.

DEFINITIONS

"Amorphous"—By "amorphous" as that term is used here, it is meant a material with significant amorphous character. Significant amorphous character contemplates greater than 75% amorphous content, preferably greater than 90% amorphous content, and is characterized by a broad, featureless X-ray diffraction pattern. It is recognized that a small degree of crystallinity may exist in the material. However, for the amorphous precursor materials of the present invention, it is preferable that the degree of crystallinity be less than that desired in the product material.

"Bioactive"—"Bioactive" refers to a material that induces hard tissue formation in and about the implant. When implanted in soft tissue, the bioactivity may also require the presence of a growth or trophic factor, or the seeding of the implant with a hard tissue forming cell type.

"Biocompatible"—The term "biocompatible", as used herein, means that the material does not elicit a substantial detrimental response in the host. There is always concern, when a foreign object is introduced into a living body, that the object will induce an immune reaction, such as an inflammatory response that will have negative effects on the host. For example, although hydroxyapatite is generally considered to be "biocompatible", significant inflammation and tissue necrosis have been observed when crystalline hydroxyapatite microcarriers are inserted intramuscularly in animals (see, for example, Intema et al., *Int. J. Pharm* 112:215 (1994))).

"Bioresorbable"—"Bioresorbable" refers to the ability of a material to be resorbed in vivo. "Full" resorption means that no significant extracellular fragments remain. The resorption process involves elimination of the original implant materials through the action of body fluids, enzymes or cells. Resorbed calcium phosphate may, for example, be redeposited as bone mineral, or by being otherwise reutilized within the body, or excreted. "Strongly bioresorbable", as that term is used herein, means that at least 80% of the total mass of material implanted intramuscularly or subcutaneously is resorbed within one year. In preferred embodiments of the invention, the strongly resorbing PCA calcium phosphate is characterized in that, when at least 1 g (preferably 1–5 g) of PCA material is implanted at a subcutaneous or intramuscular site, at least 80% of the material is resorbed w/in one year. In more preferred embodiments, the material will be resorbed within nine months, six months, three months, and ideally one month. Furthermore, particularly preferred materials are characterized in that they can be fully resorbed in the stated time periods. For the purpose of this disclosure, "weakly" resorbable means that less than 80% of the starting material is resorbed after one year.

"Effective Amount"—An effective amount of a supplemental material is an amount sufficient to impart the desired mechanical or chemical property to the composite.

"Hardening"—"Hardening" refers to the process by which the hydrated precursor is transformed into a hardened PCA material. The PCA material is considered to be "hardened" when it is a substantially non-formable solid. Such a hardened PCA material has minimal compressibility and tends to undergo plastic as opposed to elastic deformation.

"Hydrated precursor"—The term "hydrated precursor", as used herein, refers to the paste or putty formed by hydration of the dry PCA precursors in the presence of a limited amount of aqueous solution (i.e., less than approximately 1 mL aqueous solution/1 g precursor powder). The hydrated precursor may comprise both reactants and products, in various combinations, depending on the extent to which the conversion has progressed. Both the "injectable" and "formable" PCA precursor pastes described herein are hydrated precursors. Preferred "injectable" hydrated precursors have a consistency appropriate for delivery through an 18 gauge needle.

"Poorly crystalline apatitic calcium phosphate", "PCA calcium phosphate" and "PCA material", as those terms are used herein, describe a synthetic poorly crystalline apatitic calcium phosphate. The PCA material is not necessarily restricted to a single calcium phosphate phase provided it has the characteristic XRD and FTIR pattern. A PCA calcium phosphate has substantially the same X-ray diffraction spectrum as bone. The spectrum is generally characterized by only two broad peaks in the region of 20–35° with one centered at 26° and the other centered at 32°. It is further characterized by FTIR peaks at 563 cm$^{-1}$, 1034 cm$^{-1}$, 1638 cm$^{-1}$ and 3432 cm$^{-1}$ (±2 cm$^{-1}$). Sharp shoulders are observed at 603 cm$^{-1}$ and 875 cm$^{-1}$, with a doublet having maxima at 1422 cm$^{-1}$ and 1457 cm$^{-1}$.

"Promoter"—The term "promoter", as used herein, describes a material or treatment that promotes hardening of a hydrated precursor and may enhance the ACP to PCA calcium phosphate conversion. Some promoters participate in the conversion and are incorporated into the product PCA material; others, known as "passive" promoters, do not participate.

"Reactive"—"Reactive" is used herein to refer to the ability of an amorphous calcium phosphate when mixed with liquid to form a hydrated precursor to undergo conversion to the PCA material of the present invention in the presence of a promoter in association with hardening of the precursor materials. Preferred ACPs are characterized by an ability to convert completely, an ability to convert quickly with hardening, an ability to undergo conversion with otherwise inert compounds and/or an ability to convert into a substantially homogeneous PCA material. Where the ACP is reacted with a second calcium phosphate, the "conversion" can encompass conversion of both the ACP and the second calcium phosphate. The degree of hardening and the kinetics of the hardening process are also important elements of reactivity. Some ACPs are more reactive than others. An ACP is considered "highly reactive" if it undergoes conversion and hardening to a PCA material in the presence of a weak promoter, such as dicalcium phosphate dihydrate ("DCPD") with a grain size distribution containing a significant fraction of grains greater than 100 μm. Preferred highly reactive ACPs produce a hardened PCA material in the presence of weakly promoting DCPD and water at 37° C. in less than twelve hours, with hardening being substantially complete in about one to five hours, and ideally 10–30 minutes.

BRIEF DESCRIPTION OF THE DRAWING

The invention is understood with reference to the following figures, in which.

DETAILED DESCRIPTION OF THE INVENTION

Figure 1:
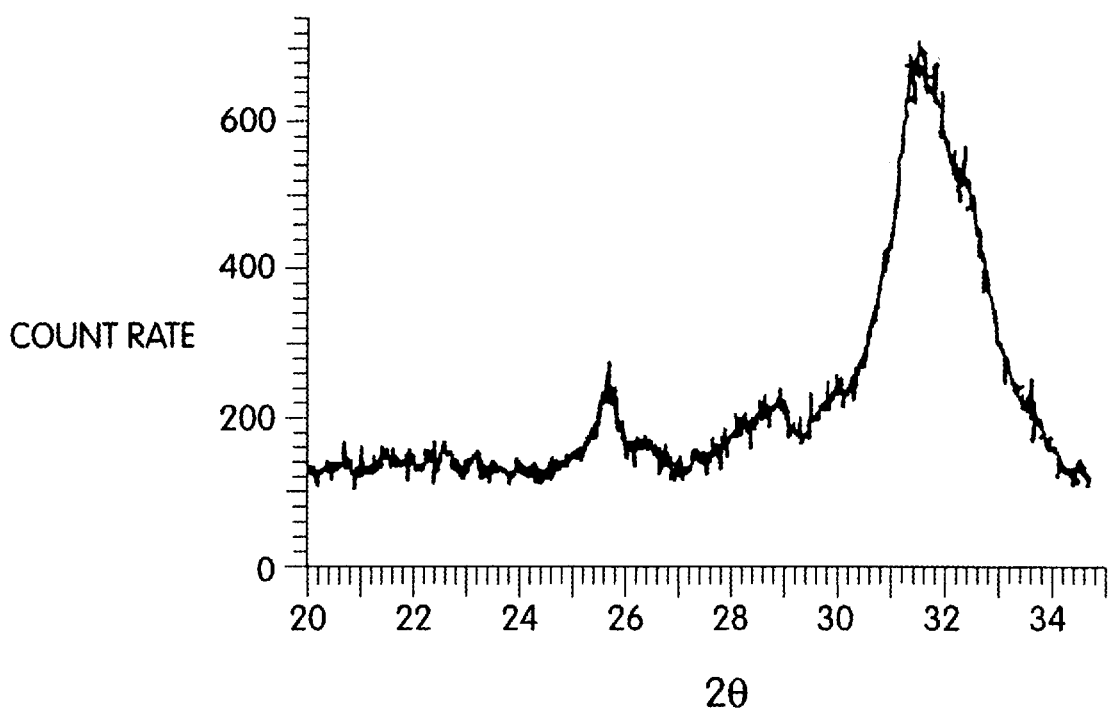
FIG. 1 is an X-ray diffraction pattern of naturally occurring bone.

The present invention is directed to the use of a strongly bioresorbable ceramic material in the repair and growth promotion of bony tissue, i.e., as a bone substitute material. In one aspect, an orthopedic or dental implant is introduced into an implant site and is demonstrated to exhibit strong bioresorbability, excellent reossification and bone ingrowth of both cortical and tribecular bone at the implant site. The orthopedic or dental implant of the present invention is comprised of a synthetic, strongly bioresorbable poorly crystalline apatitic calcium phosphate material. In preferred embodiments, it is the material described in co-pending applications U.S. Ser. No. 08/650,764 and/or U.S. Ser. No.

08/446,182, and/or the application entitled "Method and Products Related to the Physical Conversion of Reactive Amorphous Calcium Phosphate" filed on even day herewith, each of which is incorporated herein by reference.

The current invention employs a strongly bioresorbable and reossifying PCA calcium phosphate as an implantable bioceramic for the treatment of bone and dental disorders and injuries and other biological applications. The implant is useful in a variety of treatments. By way of example and in no way limiting of the invention, the ceramic material may be applied to bone-contacting surfaces of prosthetic devices, for use as a bone cement. It may be applied directly to bone defects as a filler, where it is capable of promoting the growth of new bone tissue. It may be applied to a tooth socket to avoid problems associated with tooth extraction such as dry socket and/or to provide a fixed substrate on which to anchor a replacement tooth. Alternatively, the PCA material may be used to fabricate fixtures or devices such as screws and plates, which will be resorbed and replaced by bone. When a pharmaceutically active component is added to the composite, such as growth factors or antibiotic, it serves as a drug delivery device. Release of the agent may occur over a long period of time after implantation as the PCA material slowly biodegrades. See, related co-pending application filed on even day herewith and entitled "Delivery Vehicle" which is hereby incorporated by reference.

An implant prepared using the inventive PCA material is strongly bioresorbable, that is, at least 80% of the mass of the implanted PCA material is resorbed within one year of implantation. By modifying the characteristics of the PCA material, i.e., porosity, composition, crystallinity, etc., the resorption profile may be modified so that at least one gram (preferably 1–5 grams) of the PCA material is at least 80% resorbed within 12 months, 9 months, 6 months, 3 months or ideally, 1 month, from implantation.

In addition the implant prepared from the inventive PCA calcium phosphate strongly promotes ingrowth of new bone into the implant site. Many current bone implant materials, e.g., bioresorbable organic polymer, merely promote bone apposition at the implant surface. In contrast, the implant of the present invention promotes the growth of new bone within the implant itself. Growth of both trabecular bone and cortical bone (outer bone layer) has been demonstrated to occur. Significant ingrowth occurs within days of implantation. Substantially the entire implant site has been subsumed by new bone within six months and ideally within one month, of implantation. Weight-bearing bones tend to regenerate bone more rapidly than non-load bearing bones. Thus, ingrowth for the latter may occur somewhat more slowly.

The inventive PCA calcium phosphate undergoes ossification. Ossification refers to the replacement of the implanted synthetic calcium phosphate with bone which histologically is similar or identical to natural bone. Ossification of the inventive PCA calcium phosphate tends to occur in stages with more unorganized bone appearing prior to the establishment of more natural appearing tissue. The inventive PCA calcium phosphate is different from previous bone fillers and cements because bone formation does not occur only at the outer edge of the implant, but initiates simultaneously throughout the implant, presumably in association with the resorptive process. Within two to three weeks following implantation of the PCA material into a load bearing region, such as the tibia or radius, preliminary ossification is observed by the formation of small foci of mineralized osteoid formation (spicules). By four weeks, the spicules have given way to lacy appearing thin cancellous trabecular bone and thin cortical bone. At six weeks, ordered normal or thicker than normal compact cortical bone with lacunae-containing osteocytes is observed. At time points after six weeks, final remodelling occurs so that by twelve weeks the newly ossified bone is indistinguishable from native bone.

Thus, ossification in the presence of PCA calcium phosphate generally reaches completion and appears to occur more rapidly than normal bone growth. This rapid rate of ossification suggests the inventive PCA calcium phosphate enhances bone healing. New bone is observed as early as two weeks and may reach the fully histologically organized state within six weeks, but in any case by 3–6 months. In sheep segmental defect fracture models employing implants of up to 3 gms of hydrated precursor, bone having 100% of the strength of non-fractured bone was found within three months. In the presence of trophic or growth factors such as bone morphogenic proteins this process may be accelerated.

In preferred embodiments, in order to optimize ossification, devices, pastes and putties of the invention may be seeded with bone forming cells. This is most easily accomplished by placing the device (containing PCA calcium phosphate or a hydrated precursor thereto) in contact with a source of the patient's own bone forming cells. Such cells may be found in bone-associated blood or fluids, including exogenous fluids which have been in contact with bone or bone materials or regions, including the periosteum, cortical bone, cancellous bone or marrow. They are also present in tissue including cortical or cancerous bone, bone marrow or periosteum. In the case of devices such as screws and pins, the introduction of which into bone is accompanied by bleeding, no further seeding is required. For plates, which oppose only cortical bone, induction of a periosteal lesion which will contact the device is recommended. In yet other embodiments, it will be useful to surgically prepare a seating within the bone by removing a portion of cortical bone at the implant site. Other steps may also be taken to augment ossification, including introduction of bone forming cells harvested from the patient into the graft, or incorporation of trophic factors or bone growth inducing proteins into, or onto the device. Non-autologous bone cells are also within the scope of the invention if the desired amount of bone regeneration occurs prior to host rejection of the bone forming cells. Thus, cells or tissues obtained from primary sources, cell lines or cell banks may all be useful in certain embodiments. Similar considerations apply for cartilage formation and healing and the seeding of the inventive PCA calcium phosphate with chondrocytes and/or other cartilage forming cells.

The implant also prevents deleterious reactions from occurring within the bone gap. For example, fibrous tissue often forms at bone defect sites, which impairs the ingrowth of bone. The implant of the invention is biocompatible and has been demonstrated to reduce the incidence of fibrotic growth at bone defects.

The orthopedic or dental implant of the present invention may be implanted in a patient in a paste or putty form (i.e., as a hydrated precursor). Since the inventive reaction that produces the PCA material can be initiated outside the body, and proceeds slowly at room temperature, the possibility that the material will "set up" prior to application to the surgical site and become unusable is minimized. The reaction accelerates significantly at body temperature and the material hardens in place. This feature is particularly useful in the surgical setting, where custom fitting of the device to the implant location is typically required. Alternatively, the inventive orthopedic or dental implant may be pre-hardened outside the body and implanted at a later time. This approach is useful in those situations where custom shapes are not essential, and where production of large numbers of implants is desired.

Preparation of reactive amorphous calcium phosphate used in the preparation of PCA calcium phosphate. A reactive amorphous calcium phosphate (ACP) is desirably used to form a poorly crystalline, synthetic apatitic calcium phosphate that provides bioactivity, bioresorbability and structural integrity to the above-described implants. This novel amorphous material can be converted at 37° C. (as well as temperatures above and below 37° C.) to form a bone-like material consisting of PCA calcium phosphate. This amorphous calcium phosphate is highly reactive towards other calcium phosphates and is capable of reacting at room temperature with a variety of calcium- or phosphorus-bearing compounds which are not conventionally considered to be reactive to ACP, for example CaO, $CaCO_3$ and calcium acetate. By "amorphous" as that term is used herein it is meant a material with significant amorphous character. Significant amorphous character contemplates greater than about 75% amorphous content and preferably greater than about 90% amorphous content and is characterized by a broad, featureless X-ray diffraction pattern. It is recognized that a small amount of crystallinity may exist in the material, however, it is anticipated that the crystallinity will not be greater than the degree of crystallinity desired in the product PCA calcium phosphate.

Figure 2:
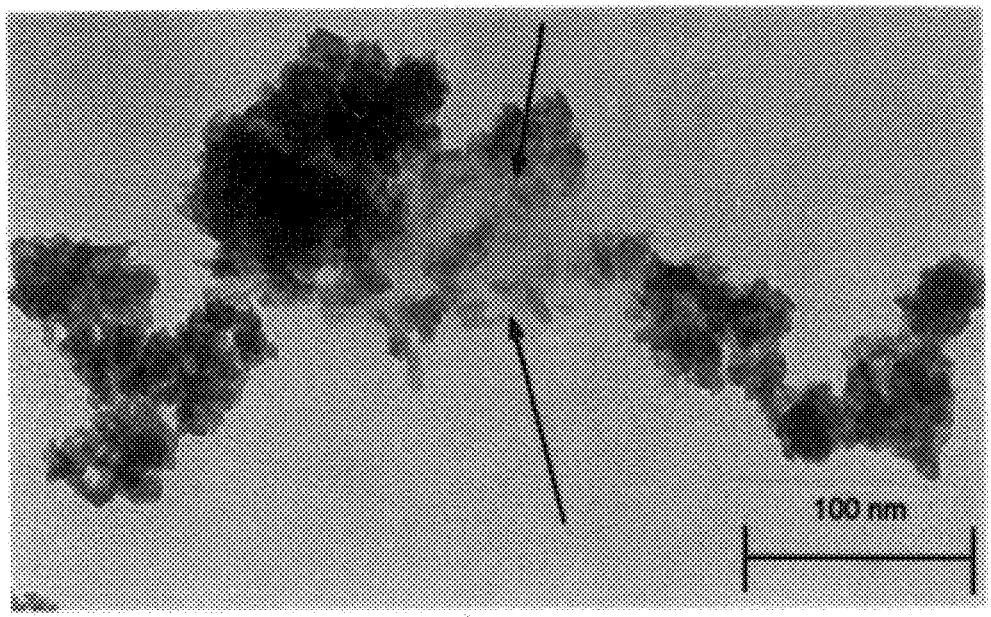
FIG. 2 is a high-resolution transmission electron micrograph of the reactive amorphous calcium phosphate illustrating the nanometer-sized grains in clusters with relatively unclear boundaries and partially immersed in shapeless form (arrows)

ACP particles of less than 1000 Å, preferably 200–500 Å, and most preferably 300 Å, are initially formed, the further growth of which are curtailed by rapid precipitation of the product from solution. In FIG. 2, a high-resolution transmission electron micrograph of the ACP precipitate is shown to illustrate the morphological characteristics and the angstrom-scale nature of the preferred reactive amorphous calcium phosphate. Note the unclear boundaries separating the globule-like clusters, lacking clear edges and surfaces, in contrast to crystalline material.

During reaction of calcium and phosphate ion sources to form an ACP, a third ion may be introduced in the solution so that these ions are incorporated in the amorphous precipitate structure instead of trivalent $PO_4^{3-}$ group(s). Because some $PO_4^{3-}$ is replaced by the third ion, the overall $PO_4^{3-}$ decreases, thus increasing the Ca/P ratio of the amorphous precipitate (as compared to standard amorphous calcium phosphate) and modifying the valence or charge state of the calcium phosphate. The amorphous solids then may be rapidly freeze-dried to preserve the chemical and physical properties of the material. The amorphous solids then may be treated under specific conditions selected to promote removal of at least some of the third ion. In the case of carbonate, specific temperature and pressure conditions lead to the reduction of total carbon, presumably as gaseous carbon dioxide from the amorphous solid, while maintaining the amorphicity.

In a preferred embodiment, where carbonate is present in the ACP, the ACP powder is heated to drive off remaining free water, water of hydration and to remove carbon, presumably through the decomposition of $CO_3^{2-}$ into $CO_2$ and oxygen. The heating step is carried out at a temperature less than 500°–600° C. but more than 400° C., so as to prevent conversion of the amorphous calcium phosphate into crystalline hydroxyapatite. Heating is carried out at a temperature in the range of about 300–500° C., and preferably 450–460° C., for about one to six hours. Heating for extended periods, e.g., greater than about 6 hours, has been found to degrade the ACP reactivity.

The resultant material is an amorphous solid with a higher Ca/P ratio than is typically found in amorphous calcium phosphates, which is generally reported to be 1.50. Further, removing carbon from the material is believed to result in vacancies in the interstitial structure within the amorphous solids, rendering it a highly reactive solid. There may be several possible vacancy sources. The material possesses a porosity which promotes reactivity by various means, such as increased surface area. The material may also undergo a change in the stoichiometry balance upon removal of the third ion. This stoichiometry change may result a charge imbalance which is responsible for the increased reactivity of the amorphous calcium phosphate.

It is desirable to maintain the amorphous property of the material throughout the entire process. If crystallinity in its entirety (single crystalline regions) or even in local domains (microcrystalline regions) is introduced during the process or in the final product, the solid has been found to lose its reactivity. The resultant highly reactive calcium phosphate is amorphous in nature and has a calcium to phosphorous ratio in the range of 1.55 to 1.65. In a preferred embodiment, the amorphous calcium phosphate has a Ca/P ratio of about 1.58.

Additional information on reactive amorphous calcium phosphates may be found in co-pending U.S. Ser. No. 08/446,182 filed on May 19, 1995 and entitled "Synthesis of Reactive Amorphous Calcium Phosphates" and in co-pending application U.S. Ser. No. 08/650,764, filed on May 20, 1996 and entitled "Novel Bone Substitute Material and a Method of Its Manufacture", which are herein incorporated in its entirety by reference.

Preparation of PCA calcium phosphate. The reaction to obtain PCA calcium phosphate employs at least one amorphous calcium phosphate (ACP) precursor, and preferably employs an activated or reactive ACP. In some instances, the reaction may employ only one precursor ACP which is converted in a controlled fashion in part or whole to the PCA calcium phosphate of the invention. Alternatively, the reaction may employ one or more additional precursors (preferably a calcium and/or a phosphate source), which combine with the ACP to yield the PCA calcium phosphate of the invention. Reactions which can be initiated outside of the body, carried out in a paste-like configuration and which can be significantly accelerated at 37° C. leading to a hardened calcium phosphate product are greatly preferred. The hardened PCA calcium phosphate alone has a durometer and bulk modulus similar to traditional blackboard chalk. In some instances, hardened PCA material will be associated with the presence of unreacted precursors, promoters, and/or supplemental materials, side products and by-products.

The conversion of ACP to PCA calcium phosphate typically is initiated by addition of a limited amount of water to an ACP powder sufficient to prepare a paste or putty. Fluid addition is typically limited to about 1.5 ml fluid/1 g powder. As the conversion proceeds it is accompanied by hardening of the paste. The conversion of ACP to PCA calcium phosphate proceeds in a controlled and predictable fashion leading to the hardening of the PCA material.

By selecting the appropriate amount of liquid to be added to the reactant powders, the viscosity of the PCA hydrated precursor may be adjusted according to need. The hydrated precursor may be prepared either with an injectable or formable consistency. "Injectable" consistency means as thick as possible while still capable of passing through a 16 to 18 gauge needle. Most often, this will be a "toothpaste"-like which represents markedly improved flow characteristics over prior art compositions. The prior art materials generally exhibit a granular or oatmeal-like consistency.

"Formable" refers to consistency that allows the material to retain its shape. A formable hydrated precursor typically will have the consistency of glazing putty or caulking compound. The hydrated precursor also may be prepared with just enough liquid to be both injectable and formable. The hydrated precursor may be prepared before use, up to a period of several hours if held at room temperature and evaporation is minimized. The storage time may be even further extended by maintaining the paste at reduced temperatures in the range of 1–10° C. and taking steps to minimize evaporative loss.

The conversion of the reactive ACP into a PCA calcium phosphate is promoted by addition of one or more "promoters" to the ACP powder. Suitable promoters may be non-participatory in that they do not participate in the reaction. Suitable non-participatory promoters include, but are not limited to, materials or treatments that have previously been described as promoting conversion of a calcium phosphate material into HA. For example, water and heat, nucleation causing substances and/or catalysts may be used as promoters. Although not bound to any particular mode of operation, it is presumed that a catalyst or nucleator provides surface area, the presence of which promotes conversion of ACP into the PCA material. Additional suitable non-participatory promoters include $Al_2O_3$, mica, glass and sand. Non-participatory promoters are desirably insoluble or poorly soluble in water, are in granular form with a particle size in the range of 1–200 micrometers, and, optionally, are bioresorbable.

When amorphous calcium phosphate is used as the sole precursor to produce a resorbable bioceramic material, it is important to control the natural tendency of the ACP to convert to highly crystalline hydroxyapatite. On the other hand, the time course of conversion should be fast enough to have surgical utility. One approach is to combine a precursor ACP containing an inhibitor of crystal formation with an ACP that does not contain an inhibitor of crystal formation (e.g., a promoter). The reactants may be mixed in a dry state, with the appropriate particulate size and an excess of the inhibitor-containing ACP. The reactants can then be hydrated by addition of water, followed by an elevation in temperature, such as that which occurs following introduction into the body, to convert the reactants to the PCA calcium phosphate of the invention. Particularly suitable in this regard are substances which provide reactive surfaces which weakly promote apatitic crystallization to produce a poorly crystalline apatitic calcium phosphate.

The amorphous calcium phosphate powder of the present invention may be mixed with a variety of participatory promoters which react to form the PCA material. This reaction preferably occurs at patient body temperature upon mixing of the ACP powder with calcium phosphates in the presence of a fluid, such as but not limited to, water, saline, buffer solution, serum or tissue culture medium. Depending upon the amount of fluid added the mixture of amorphous calcium phosphate of the present invention and acidic calcium phosphate results in a highly formable and/or highly injectable paste (i.e., hydrated precursor) with varying degrees of consistency depending upon the exact formulation used. The ACP precursor may be reacted with a second calcium source (including a second ACP) using any reaction promoting technique. Such reactions include acid/base, displacement, substitution, and hydrolysis reactions as well as purely physical and mechanical reactions.

Under any reaction scheme it is important that the ACP retains significant amorphous character throughout the reaction. Specifically, the overall crystallinity within the starting ACP does not exceed that desired in the end product. Thus certain reaction schemes may require stabilization of the amorphous nature of the ACP throughout the reaction period. Examples of suitable crystallization inhibitors known to the art include carbonate, magnesium and pyrophosphates. Additional guidance for the use of inhibitors of crystallization may be found in LeGeros, Ibid. and Elliot, Structure and Chemistry of the Apatites and other Calcium Orthophosphates, Elsevier, Netherlands, 1994, herein incorporated by reference. Other methods of activation known to the art, such catalysis or the use of ionic solvents or promoters of nucleation, may also be used to promote reaction between substituents. In many forms of the current invention, at least one of the precursors must be activated so as to react with the other components at physiological conditions as described hereinabove.

Appropriate calcium phosphates include both basic and acidic calcium phosphates which provide the appropriate stoichiometry for reaction to obtain a PCA calcium phosphate. Suitable calcium phosphates include, but are in no way limited to, calcium metaphosphate, dicalcium phosphate dihydrate, heptacalcium decaphosphate, tricalcium phosphates, calcium pyrophosphate dihydrate, crystalline HA, PCA calcium phosphate, calcium pyrophosphate, monetite, octacalcium phosphate and ACP. In one embodiment, an acidic (pH 5–7) calcium phosphate is used. In another embodiment, the inventive PCA calcium phosphate is used in particulate form as the second component. In yet another embodiment, fine particulate crystalline HA is used as the second component. Other solids which provide a source of phosphate or calcium, such as by way of example only, CaO, $CaCO_3$, calcium acetate, and $H_3PO_4$, may be mixed to form a final product to yield a desired Ca/P ratio close to natural bone. The second calcium phosphate reactant may be of any crystalline structure and should be chosen so as to be reactive with the first ACP either directly or through the use of a reaction promoting vehicles, such as ionic solvents or catalysts. Preferred second calcium phosphate reactants are those which tend themselves to undergo conversion to HA through an intermediate PCA calcium phosphate phase. It may be desirable to provide the second component in the amorphous or poorly crystalline state, as well. Suitable reactants and appropriate reaction conditions may be determined by mixing reactants and water, and demonstrating rapid hardening at about 37° C.

Figure 3A:
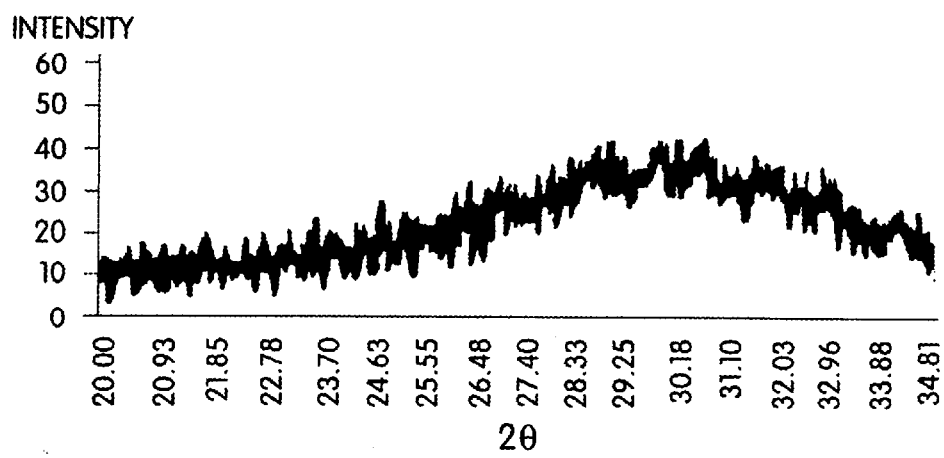
FIG. 3 shows X-ray diffraction patterns of (a) a reactive amorphous calcium phosphate; and (b) a dicalcium diphosphate and (c) the product poorly crystalline apatitic calcium phosphate.
Figure 3B:
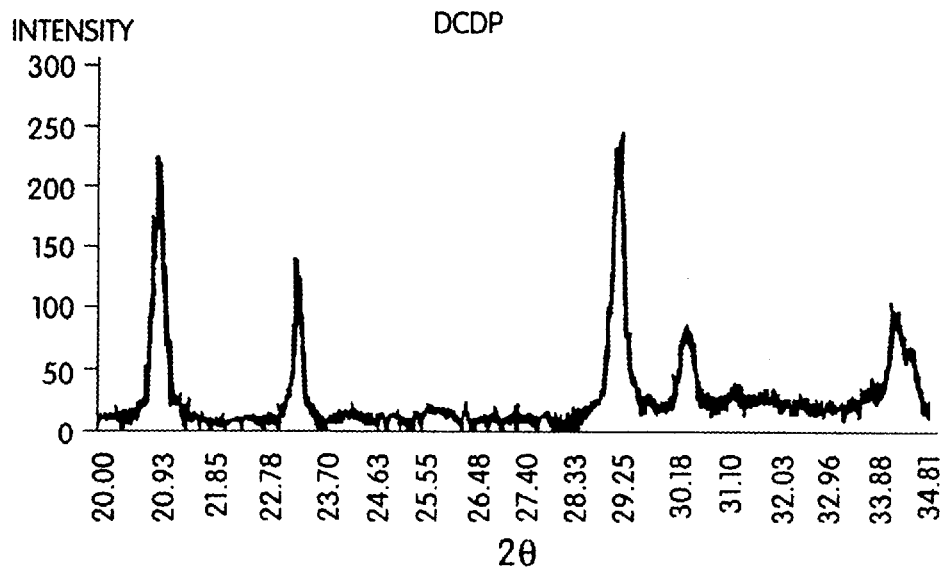
Figure 3C:
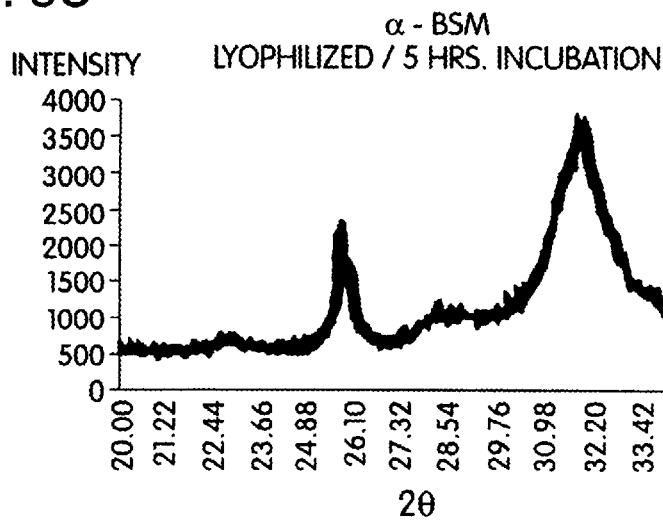

The second calcium phosphate is often crystalline, as is evidenced by the presence of sharp diffraction peaks of a typical calcium phosphate reactant, DCPD, as shown in the X-ray diffraction pattern (FIG. 3(a)). In contrast, the reactive ACP is amorphous and shows no identifiable peaks by X-ray diffraction (FIG. 3(b)). Despite its higher crystallinity, however, in a preferred embodiment DCPD is consumed in the reaction with reactive ACP and the product PCA calcium phosphate is of much reduced crystallinity (FIG. 3(c)), as compared to DCPD.

Because at least one of the reactants is amorphous and highly reactive, the reaction proceeds at room or body temperature to provide an apatitic material having a poorly-crystalline or microcrystalline microstructure. The reaction also is substantially complete, thereby insuring that all calcium and phosphate of the mixture are consumed by the resultant apatitic product. This permits reliable manufacture of PCA calcium phosphate simply by selection of the relative proportions of the starting amorphous and secondary calcium phosphates. It is desirable to maintain a calcium to phosphate ratio of about 1.2–1.68, preferably less than 1.5, and most preferably about 1.38.

The PCA calcium phosphate of the invention is characterized by its biological resorbability, ability to promote bone ingrowth and substantial absence of crystallinity. Its crystalline character is substantially the same as natural bone, as compared to the higher degree of crystallinity seen in the bone substitute materials known to the art. The inventive PCA calcium phosphate also is biocompatible, that is, no significant detrimental reaction (e.g., inflammation or fibrosis) is induced in the host by the implanted composite material. Materials which induce a medically acceptable level of inflammation or fibrosis are considered biocompatible.

The resorbability of the PCA material employed in the instant invention is attributable to the combination of its porosity, density, chemical composition, reaction conditions and crystallinity. Apatites have reduced crystalline characters and display somewhat increased solubility in aqueous systems when compared with more crystalline species. The low crystallinity of the inventive PCA material, and/or the presence of stable amorphous domains within it, is believed to promote its resorbability in biological systems.

The resorbability of the PCA material of the present invention can be modified by altering its porosity. Porosity facilitates both the diffusion of substances to and from the material and, in certain applications, the penetration of cells and cell processes into the material matrix, thereby allowing sufficient bone ingrowth into the device. Implant devices of lower porosity resorb more slowly in vivo than do those of higher porosity. In one embodiment of the invention, porosity is increased through the use of controlled particle size reactants. In other embodiments, chemical or physical etching or addition of leaching agents, such as sugars, salts and bioerodible polymers may be employed to provide a desired level of porosity.

The PCA material may be formulated as a composite for use as an implant according to the invention, thereby improving the mechanical properties of the material. In some formulations, the hardened PCA calcium phosphate alone is brittle and has a durometer and bulk modulus similar to traditional blackboard chalk. The preparation of PCA calcium phosphate as a composite material is desirable in order to alter the mechanical properties for some medical uses. Furthermore, the consistency, formability and hardness of the PCA calcium phosphate, as well as the reaction speed, may be varied according to the therapeutic need by selection of the appropriate supplementary materials from which to prepare the implantable bioceramic composite material of the invention. The ceramic composite implant may be formulated to improve strength for load bearing applications, or to improve adhesive strength for cementing applications. See, related application filed on even day herewith and entitled "Bioresorbable Ceramic Composite" and hereby incorporated by reference.

Method of application of the implant to bony sites. The implant of the invention may be prepared outside the body in a variety of forms and introduced into the patient at the implant site using methods appropriate to the form of the implant and nature of the malady.

In one embodiment, the implant may be prepared as an injectable paste. A liquid is added to precursor powders to form an injectable hydrated precursor which is capable of in vivo conversion into a bioresorbable PCA calcium phosphate, as described hereinabove. The precise amount of liquid will vary dependent upon the desired consistency of the paste and the nature of the precursor powders used to prepare the PCA material. Typically, about 0.75–1:1 ml liquid per gram powder is used. The paste is desirably injected into the implant site by syringe, preferably using a sixteen or an eighteen gauge syringe. In some embodiments, it may be desirable to prepare the paste ahead of time and to store the paste in the syringe at sub-ambient temperatures until needed. In some embodiments, injection by syringe into a body cavity or intermedullary space may be aided by the use of vacuum to aid in displacing fluids or gases. Most often a vacuum may be applied by insertion of a second needle in the vicinity of the intended injection site. A gentle vacuum may then be applied through the second needle. Application of the implant by injection is particularly desirable for situations in which the material is used as a bone cement to join and hold bone fragments in place or to improve adhesion of, for example, a hip prosthesis. Implantation in a non-open surgical setting is also desirable.

In another embodiment, the implant may be prepared as a formable putty. A liquid is added to precursor powders to form a putty-like hydrated precursor which is capable of in vivo conversion into a bioresorbable PCA calcium phosphate. The precise amount of liquid will vary dependent upon the desired consistency of the putty and the nature of the precursor powders used to prepare the PCA material. Typically, less than about 1.0 ml liquid per gram powder is used. The hydrated precursor putty may be prepared and molded to approximate the implant shape. The putty may then be pressed into place to fill a gap in the bone, tooth socket or other site. Use of a bone putty may be particularly desirable in repair of bone defects in non-union bone or other situations where the gap to be filled is large and requires a degree of mechanical integrity in the implant material to both fill the gap and retain its shape.

In yet another embodiment, dry precursor powders may be applied directly to a bone defect. Hydration and conversion of the precursor into the PCA material occurs at the bone defect site by direct exposure to blood or other physiological fluids. Such application may be particularly desirably where the bone defect is accompanied by excessive bleeding. The hydroscopic nature of the precursor powders serves to absorb body fluids, provide a physical barrier to protect the wound site and to provide a bone substitute material which promotes bone in growth at the defect site.

In still yet another embodiment of the invention, the implant may be prepared from a prehardened PCA calcium phosphate which has been shaped into the desired form. This may be accomplished by preparing a hydrated precursor as a putty or paste as described above, injecting or pressing the hydrated precursor into a mold, and allowing the precursor material to convert and harden into the PCA calcium phosphate. Alternatively, the PCA calcium phosphate may be prepared as a solid block or other such geometry and shaped into the desired object using drills or other such shaping tools known in the art. This method is particularly desirable for production of resorbable objects such as anchors for tooth implants, spacers for cervical fusion, resorbable screws and plates, and slowly resorbably shapes for augmentation.

Orthopedic and dental implants. The implants described hereinabove may be useful in the treatment of a variety of orthopedic and dental disorders. The materials used in the preparation of the implant are desirably sterile and may be sterilized using conventional techniques, including by not limited to gamma irradiation, filtration, and ethylene oxide.

Healing of bone fractures and defects. PCA calcium phosphate may be used to join two or more bone pieces together and/or to improve healing of bone fractures by filling the gap left by the fracture, or space caused by compressive damage as a result of the fracture.

Figure 4:
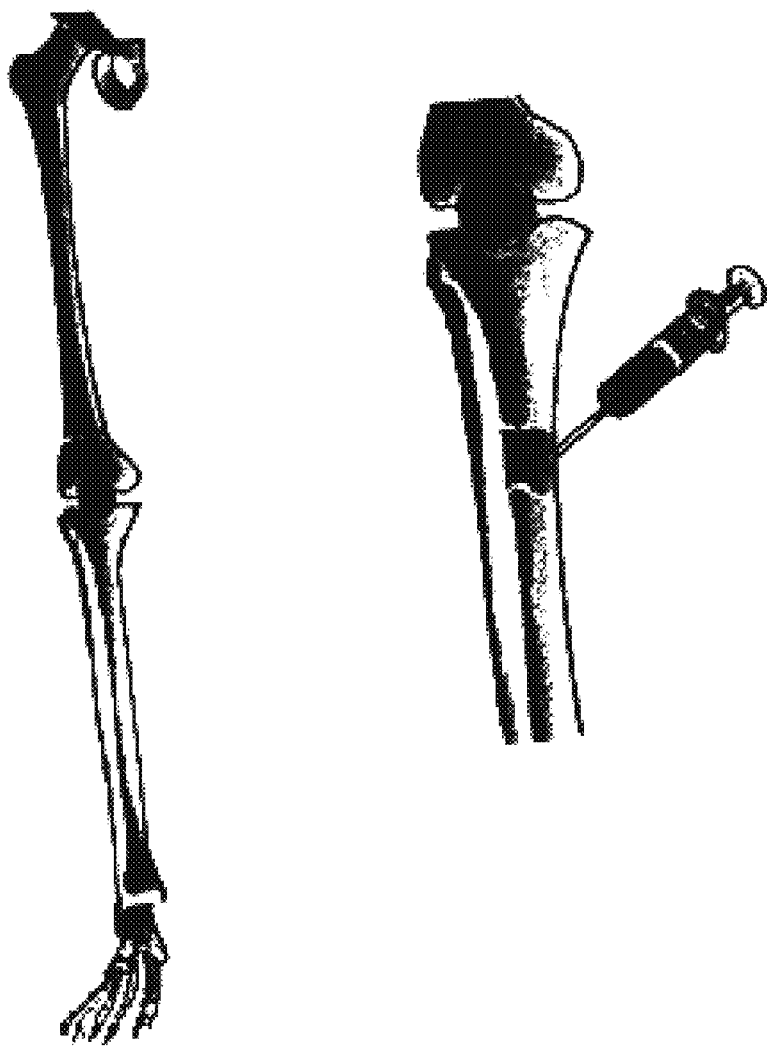
FIG. 4 is a pictorial illustration of an implant of the invention introduced into a non-union bone site.

In the situation involving non-union bone fractures, the implant can be used to stabilize the bone defect because the implant hardens in place in vivo. The implant of the invention is especially advantageous in that the bone gap can be filled without open surgery. To this end, the bone defect site may be observed by x-ray to ensure proper positioning of the injection needle. The implant may then be directly injected into the defect site. X-ray or MRI visualization may be used, if desired, to confirm placement. FIG. 4 is a pictorial illustration of application of the implant to a tibial defect in which the implant material is injected into the bone defect. When the gap is particularly large, it may be desirable to first immobilize or "fix" the defect and then fill the gap with implant material. The defect may be fixed using conventional fixation devices, such as titanium screws, pins and plates. In preferred embodiments, the defect is fixed with screws or plates prepared from hardened PCA material and/or composites thereof, which are themselves bioresorbable and hence allow complete bone ingrowth at the defect site and require no post surgical treatment to remove the hardware.

Figure 5:
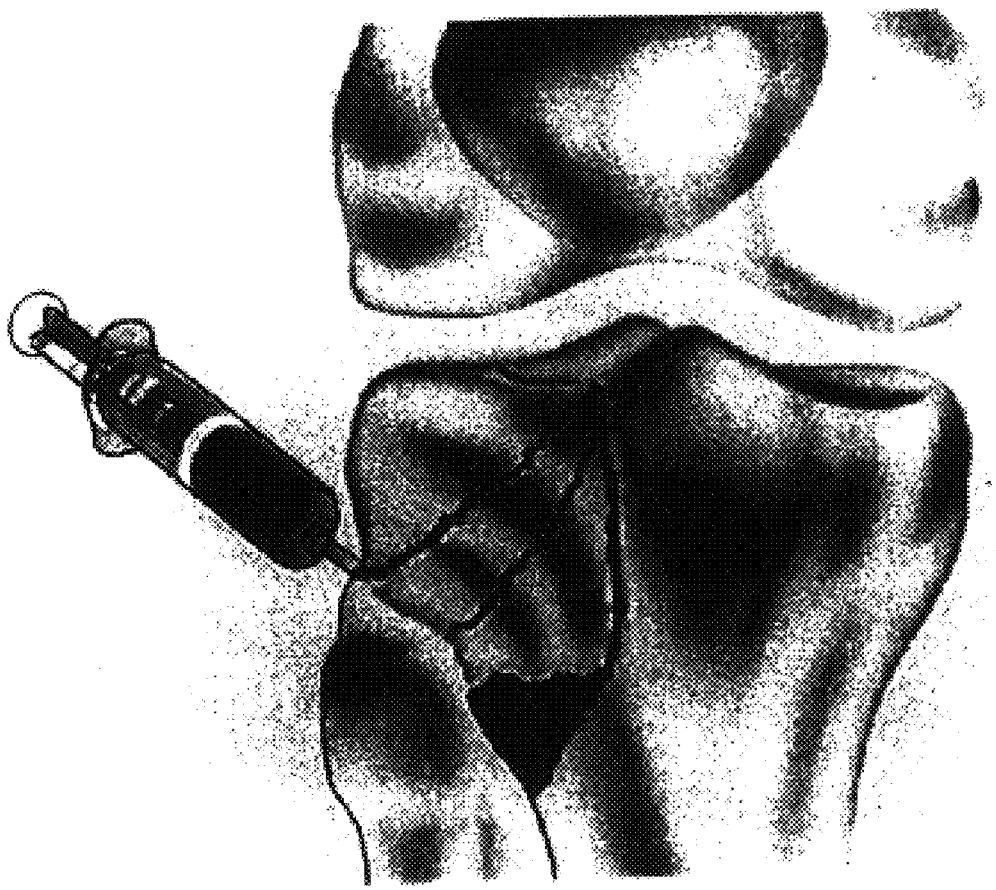
FIG. 5 is a pictorial illustration of an implant of the invention introduced into a fragmented bone site.

In the situation where the bone has been crushed or fragmented, the bone fragments may be reassembled and the implant material may be used to hold them in place while a bone matrix regrows at the fracture site. FIG. 5 is a pictorial illustration of a fragmented bone which has been reassembled. Hydrated precursor paste is injected around the bone fragments which are held rigid once the paste converts into PCA calcium phosphate. Bone regrowth occurs to regenerate bone tissue and imbed original bone fragments in new bone matrix.

The implant may also be used to heal compression fractions, such as compression of the tibia. The cortical bone surface can be re-aligned and fixed in place using mechanical fixation and the implant can be used to fill the void created by the compressive destruction of the bone.

In yet another embodiment of the invention, the PCA calcium phosphate implant may be used to secure pins, screws and other more complicated prosthesis devices which are used to hold bone in place. By immobilizing the fracture using hardware and embedding the hardware in PCA paste, potential voids are filled, thereby expediting new bone formation around the screw. In addition, the implant acts to distribute the force of the screw across a greater surface area, thereby reducing the likelihood of pull out or early bone resorption. This approach is used most often in repair of broken hip bones, where a hip prosthesis is used to reinforce the weight-bearing femoral neck of the femur.

Where it is desired to minimize surgical intervention, it is preferred to use the PCA material as a paste and to introduce the implant by syringe into the bone defect. Of course, where minimal intervention is not an issue, i.e., during open surgery, the implant may be used as a paste. Indeed, this may be preferred in some circumstances as the added formability of the PCA putty gives the physician increased control over the final shape of the implant device and improves implant conformity with neighboring bone surfaces.

Figure 6:
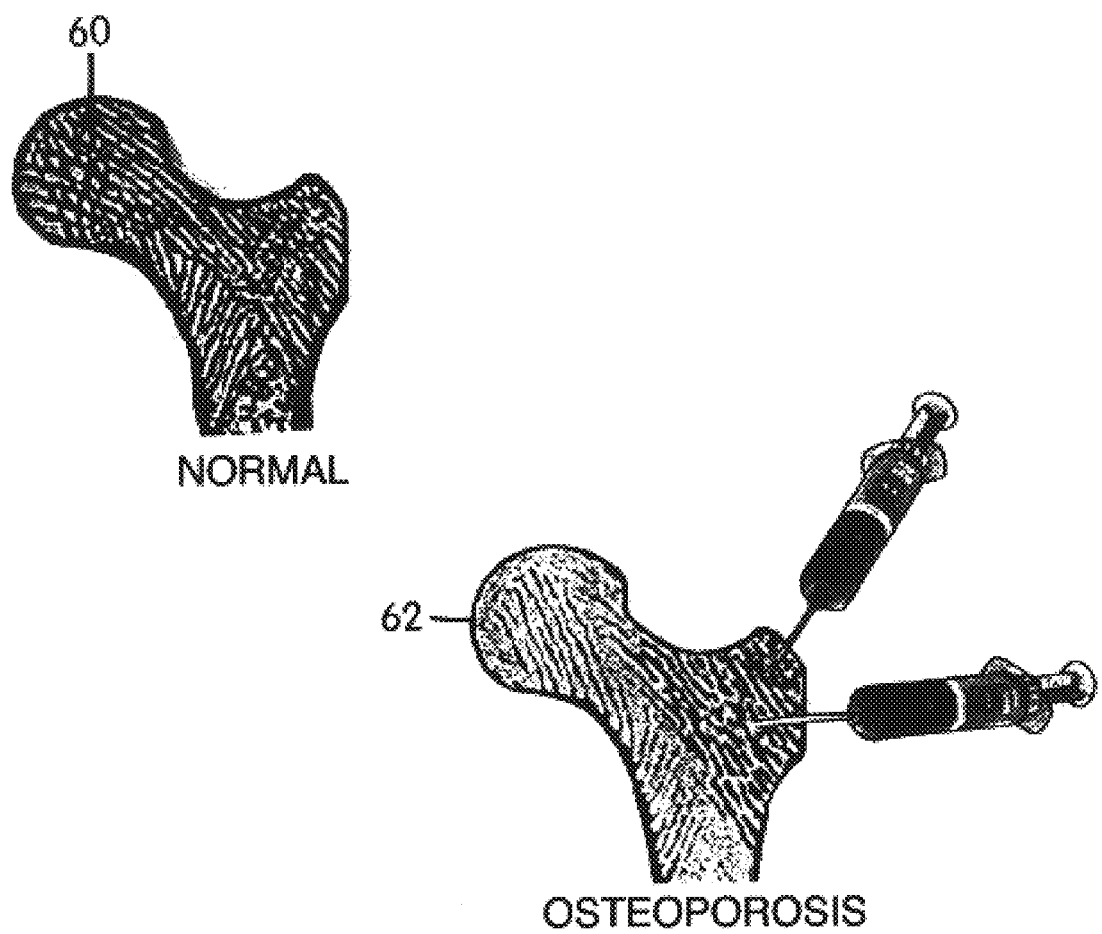
FIG. 6 is a pictorial illustration of an implant introduced by syringe into a osteoporotic bone site.

Treatment of osteoporosis. As bones age, they lose mass, thereby becoming more porous and brittle. PCA implant material may be used to promote bone growth and to densify the bone. FIG. 6 includes a pictorial illustration of a normal bone 60 having a regular and dense network of trabecular bone. FIG. 6 also illustrates osteoporotic bone 62 in which significant bone mass has been lost. Osteoporotic bone may be treated with reossifying PCA material of the invention to densify the bone and protect against bone fracture and failure. Bone strength density may be improved by injecting hydrated precursor paste into the bone interior. The precursor serves to improve bone in several ways. Firstly, the hydrated precursor hardens into PCA calcium phosphate which is strong and serves to reinforce the already brittle bone. Secondly, the PCA calcium phosphate is a biocompatible matrix accommodating and stimulating new bone growth, so that as it bioerodes, new bone is formed to replace it. Thirdly, the eroding PCA calcium phosphate is a source of bioavailable calcium for osteoblasts to use in the formation of new bone.

Figure 7:
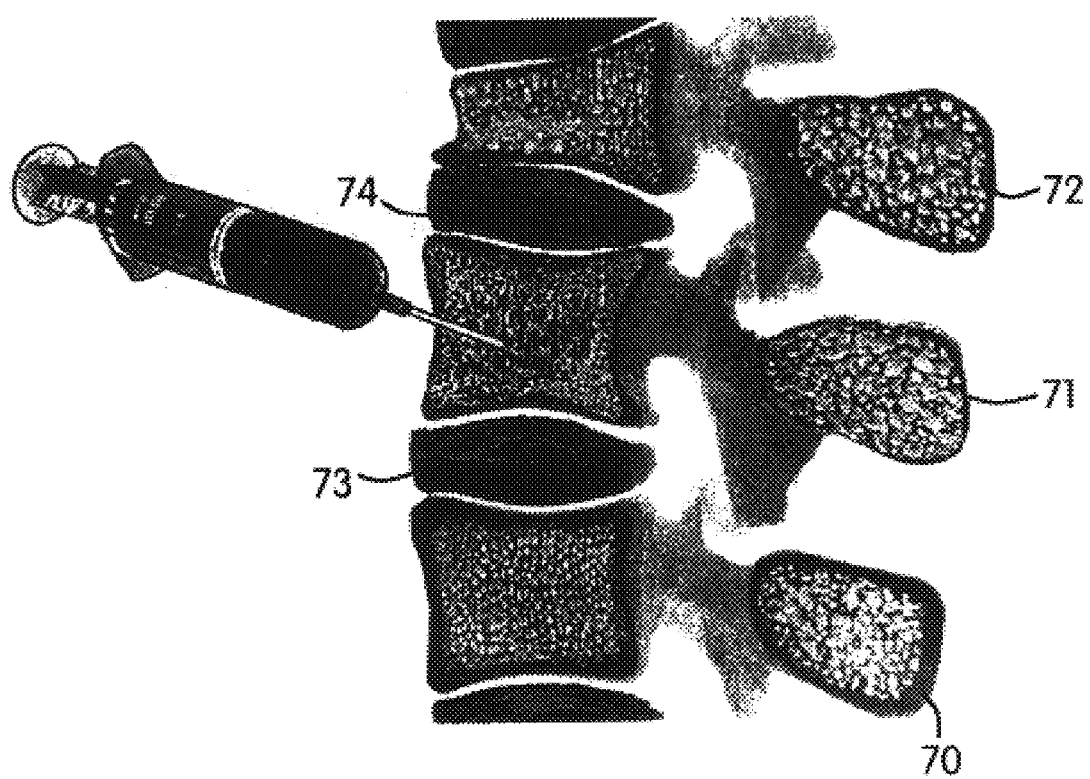
FIG. 7 is a pictorial illustration of an implant introduced by syringe into a osteoporotic vertebrae.

The implant may be particularly effective in preventing the collapse of vertebrae. FIG. 7 is a pictorial illustration of a portion of a spinal column including vertebrae 70, 71, 72 and discs 73, 74. Vertebra 70 is healthy, and exhibits dense trabecular bone matrix. Vertebra 72 is an osteoporotic vertebra which has been crushed due to increased porosity and reduced bone density. Vertebra 71 is an osteoporotic vertebra undergoing implantation of PCA calcium phosphate to strengthen bone and regenerate bone mass.

Spinal and cervical fusion. As a general rule, when discs and vertebral bodies are removed for the treatment of degenerative disease, trauma or tumor, they need to be replaced with a structural graft to maintain the patient's cervical alignment. Bone graft is usually placed as a spacer between vertebrae to facilitate fusion of vertebral bodies and to restore height. Conventional spacers, some of which are known as "cages" are made from titanium or autologous or allograft bone. However each of these prior art devices have disadvantages. Autologous bone may not always be available, allograft bone carries the risk of infection and pathogen exposure, and titanium is not resorbed by the body and either remains or must be surgically removed.

To overcome these disadvantages of the prior art implants, PCA calcium phosphate may be used as a spacer in cervical fusion procedures. The PCA calcium phosphate is prepared as a disk or shim. The PCA calcium phosphate disk may be used as a hardened, slowly resorbing spacer for the fusion of adjacent vertebrae. In preferred embodiments, the spacer is in the form of a hollow ring. The center of the ring may be filled with a PCA calcium phosphate formulated for rapid bioresorbability and bone ingrowth.

Prostheses. Prostheses for joint replacement, particularly hip replacement are widely used and can substantially improve the quality of life for the patients receiving them. However, current cementing techniques are unable to prevent all "micromotion" and gaps between the prosthesis and the natural bone receiving the implant, resulting in increased incidence of loosening and failure of the joint replacement over time with concomitant pain or discomfort to the patient.

Figure 8:
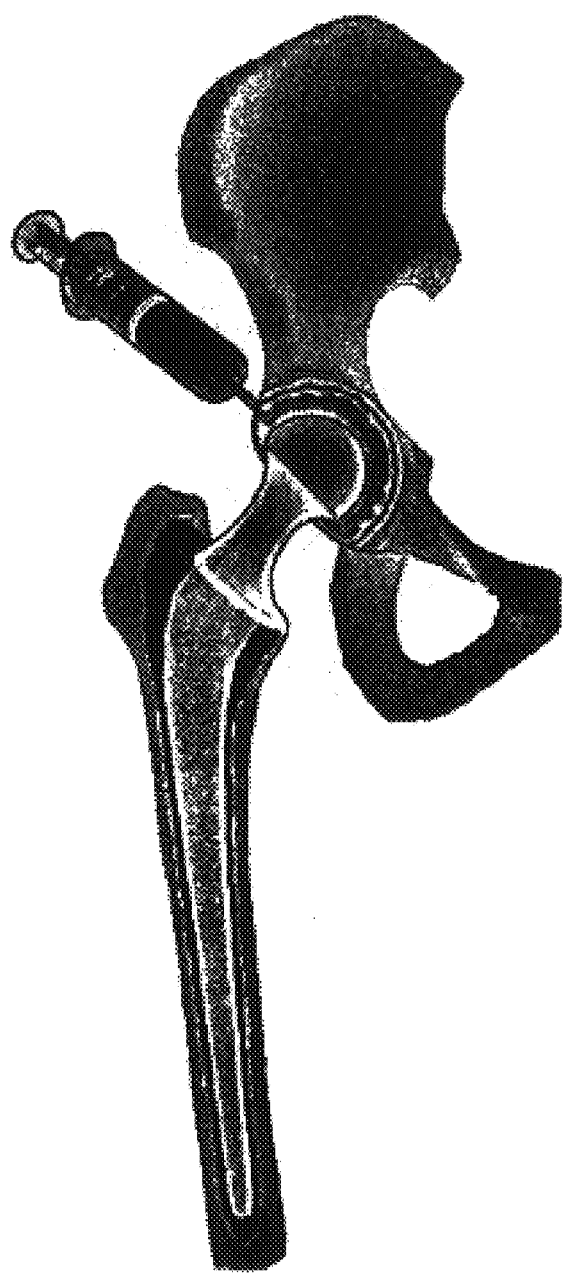
FIG. 8 is a pictorial illustration of an implant of the invention used as a bone cement to secure a hip prosthesis.

FIG. 8 is a pictorial illustration of a hip prosthesis being secured firmly into natural bone using PCA calcium phosphate as a bone cement. Thus, the hip ball and socket may be positioned in the natural bone in spaces prepared to received them. Once positioned, the hydrated precursor paste may be injected around the prosthesis to fill gaps between the bone wall and the prosthesis and to firmly cement the prosthesis to the patient's own bone. Alternatively, the bone surface may be coated with the hydrated precursor and the prosthesis may be inserted into position in the PCA material-coated bone. The hydrated precursor hardens and sets to thereby firmly anchor the prosthesis into place. In both scenarios, the PCA material slowly bioresorbs and is replaced by natural bone; thus, gaps and micromotion associated with the prosthetic device are minimalized.

In another embodiment, the prosthesis may be coated with the PCA material. Thus, a hydrated precursor may be applied to the surface of the prosthesis outside the body and is allowed to harden and convert to PCA calcium phosphate. The coating facilitates acceptance by the host of the prosthesis and promotes bone growth on the prosthesis surface.

The present implant material may also be used as an in vivo treatment of previously implanted prosthesis devices which have formed cysts at the prosthesis-bone interface. The cyst may be removed by conventional techniques, but this procedure often leaves large gaps adjacent to the prosthesis. These gaps may be filled by injection of the implant material of the invention into the gap.

Replacement material for autologous bone implants. For various reasons, the PCA material may not be preferred for use as an implant and the patient's own bone is preferred (e.g. autologous bone harvested from the patients own iliac crest). This is often the case in the treatment of bone cancer. However, the PCA material may be used at the bone removal site to rapidly promote bone regrowth at the bone harvesting site to prevent cosmetic deficiencies or create new bone for future use.

Reconstructive plastic surgery. Prehardened PCA calcium phosphate in the desired shape may be attached using hydrated precursor paste. Alternatively, a hydrated precursor paste may be formed and shaped in vivo and secured in place using hydrated precursor paste. Where synthetic bone graft is medically inappropriate, the patient's own bone may be harvested and secured at the implant site using a hydrated precursor paste or putty. As described previously, the precursor is converted into PCA calcium phosphate which is gradually resorbed and which promotes new bone growth within the implant site.

Figure 9:
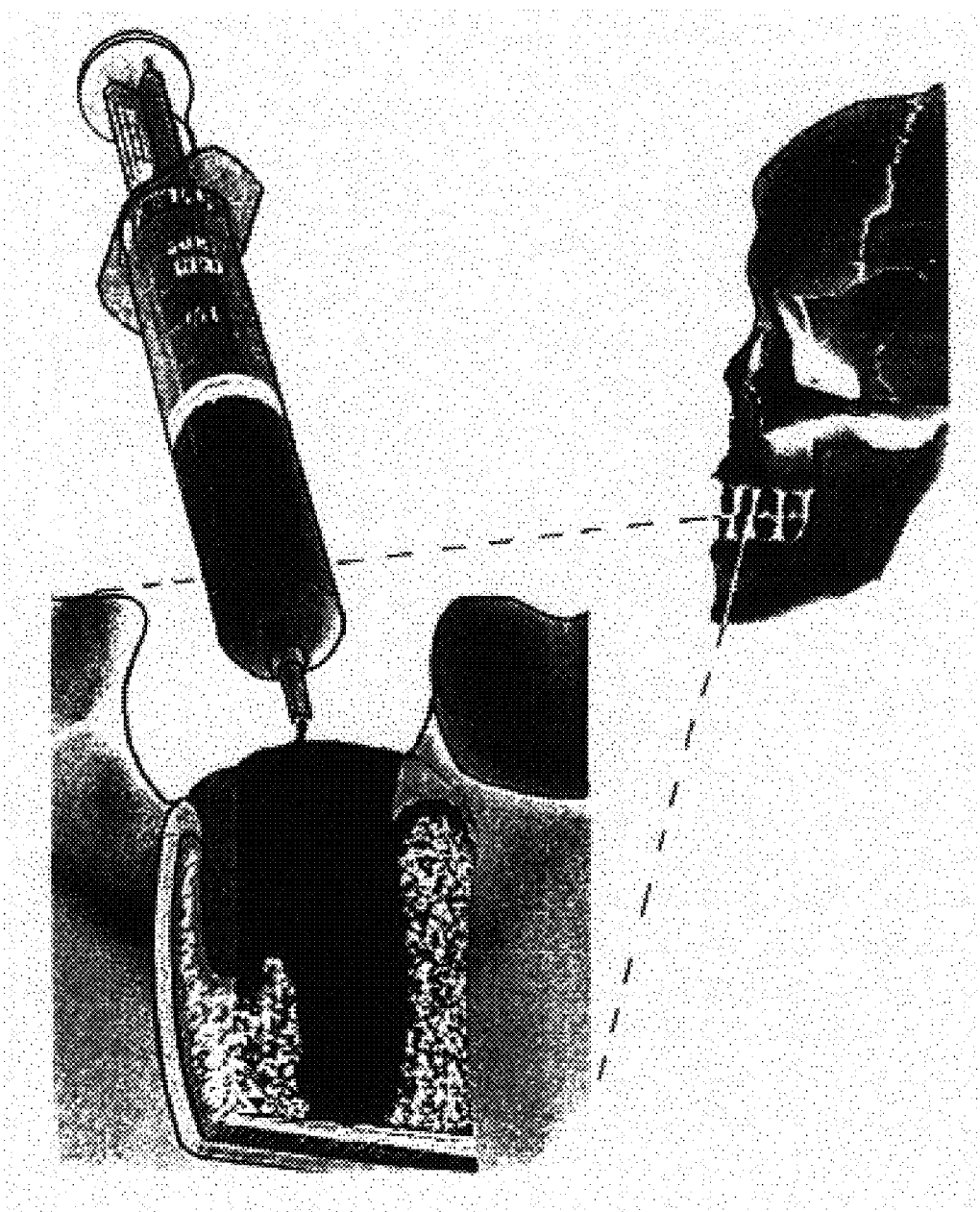
FIG. 9 is a pictorial illustration of an implant of the invention introduced into a tooth socket.

Periodontal defects. PCA calcium phosphate may be used as an implant in teeth sockets to avoid the problems associated with teeth extraction, such as dry socket, infection and fibrous growth. FIG. 9 is a pictorial illustration of a tooth socket receiving an implant by injection. The implant converts into PCA calcium phosphate and is replaced with new bone within six months, preferably within six weeks and ideally as fast as three weeks. The new bone provides an enhanced surface in which to implant dental prosthesis (replacement teeth).

Alveolar ridge defects. When, through trauma, congenital abnormalities or illness, bone loss occurs to the jaw section containing the teeth sockets (alveolar ridge), rebuilding of the ridge may be needed before dental prosthetic implantation can occur. The management of alveolar ridge deficiencies poses a challenge because the magnitude of the osseous defects are often greater than that resulting from tooth extraction and may require replacement (or regrowth) of a significant amount of bony tissue.

The conventional procedure may call for nasal floor elevation, bone grafting and bone regeneration. Bone generation prior to dental prosthesis implantation has the advantage of providing a greater bone mass for implantation and hence improved implant alignment and strength. However, the process typically occurs in staged intervals because of the length of time conventional bone regeneration requires in order to develop bone of sufficient strength to handle the bone implant. Thus, a two step technique has the disadvantage of long healing time before implant placement (ca. nine months) and poor bone quality of the regenerated tissue. See, C. M. Misch and C. E. Misch *Implant Dentistry* 4(4): 261 (1995).

The implant of the present invention allows the build-up of the alveolar ridge and dental implantation to occur over a much shorter time and often in a single step. The implant is introduced as a paste or putty to the ridge site, where it sets up and hardens in situ. Within hours or even minutes, the implant is sufficiently hard to accept the dental implant. Within six months, the implant will gradually regenerate natural bone, thereby bonding the dental implant into a hard bony site. Thus, ridge augmentation and dental prosthesis implantation may occur at the same time or within days of one another. The dental implant may also be introduced into the hydrated precursor prior to hardening. The inventive PCA calcium phosphate may also be injected into the implant in conjunction with traditional methods to increase bone ingrowth to and around the dental implant.

Figure 10:
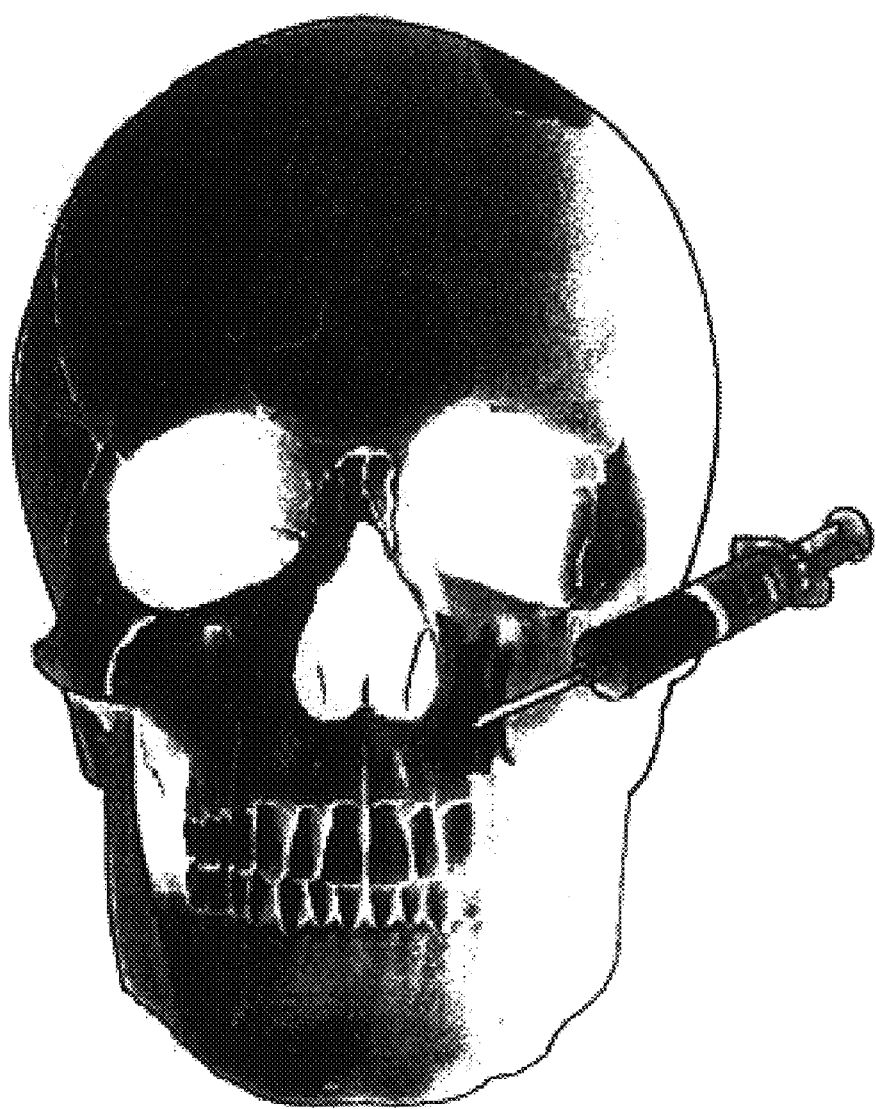
FIG. 10 is a pictorial illustration of an implant of the invention introduced into an alveolar ridge.

Likewise, the implant of the present invention may be used to augment the ridge alongside the nasal cavity, where natural bone may be too thin to accept the prosthesis. Thus, as pictorially illustrated in FIG. 10, a hole may be drilled into the alveolar ridge adjacent to the sinus cavity, the sinus sac may be raised and implant material is introduced into the site by injection and allowed to harden. With hardening and ossification, the ridge is ready for dental prosthetic implantation.

Use as a hemostatic agent. The dry precursor powder may also be applied dry as a hemostatic or absorptive agent. Once in contact with body fluids the material hydrates and then hardens in place similarly to the hydrated precursors prepared ex vivo. This property is particularly useful to control bleeding in both hard and soft tissues alike. In one application the material is applied to the opening following spinal taps or spinal surgery to form a patch and prevent CSF leaks.

Cranial repair. Cranial repair has presented a particular problem due to the slow healing of bone involved in reconstructive surgery of the cranium. The inventive PCA material may be used both to repair and to stimulate the growth of cranial bone. Additionally, growth factors or osteogenic cells may be included in the implant to further stimulate healing.

Cartilage growth. PCA calcium phosphate implants may be used to promote new cartilage growth. Cartilage forming cells (e.g. primary chondrocytes, or chondrocytic cell lines) may be used with the implant. The implant provides a matrix for cell growth and proliferation as well as a connecting means to other tissue surfaces (e.g. bone or cartilage).

To this end, the cartilage sac is ruptured and PCA calcium phosphate is injected into the cartilage site. The PCA material desirably contains chondrocytes which promote cartilage growth. For further information of cell seeding of tissue matrices, see "Cell Seeding of Ceramic Compositions" which is hereby incorporated by reference.

Temporary bony structures. The implant of the invention may be used in other than bony sites in the body. For example, an implant may be prepared from PCA calcium phosphate to be used as a protective structure for various organs of the body. According to the invention, the PCA material may be used to support, shield or frame sensitive organs. By way of example, the PCA material could be prepared outside the body as a hardened vascular stent in the treatment of heart disease or as a gastro-intestinal stent in the treatment of Krone's disease. Alternatively, the implant can be used to provide temporary support for sutured or stapled repairs, bypasses, or organ or tissue transplants and implants. The hydrated precursor may be placed around the structure in need of support, where it hardens in place providing support or mechanical protection until resorption occurs.

The invention is further exemplified with reference to the following examples, which are presented for the purpose of illustration only and are not to be considered as limiting of the invention.

EXAMPLE 1

This example describes the step-by-step preparation and methods to render relatively inert amorphous calcium phosphate solids into a highly reactive amorphous calcium phosphate.

Solution A was prepared at room temperature by the rapid dissolution of 55 g $Na_2HPO_4 \cdot 7H_2O$ (sodium phosphate), 50 g NaOH (sodium hydroxide), 30 g $NaHCO_3$ (sodium bicarbonate) in 1.3 l of distilled water. Solution B was prepared at room temperature by rapid dissolution of 43 g $Ca(NO_3)_2 \cdot 4H_2O$ (calcium nitrate tetrahydrate) in 0.5 l of distilled water.

The inert carbonated amorphous calcium phosphate was then prepared at room temperature by the rapid addition of solution B to rapidly stirring solution A. The precipitate of gel-like amorphous calcium phosphate thus formed was immediately filtered using filter paper (0.05 sq. m) with medium filter speed and a vacuum pressure of about $10^{-2}$ torr. The material formed a thin cake and was washed with approximately 4 liters of distilled water by adding water into the filtrating funnel. The washed material was then collected using spatula and immersed into a liquid nitrogen in a 2.5 L container. Following the formation of hard frozen pieces, the container was transferred into a vacuum chamber for 24 hrs ($10^{-1}$–$10^{-2}$ torr), until a fine and dry powder was obtained.

Although the procedure described above may be performed at room temperature, the entire process preferably takes place below ambient temperature (4–5° C.), so as to further prevent the amorphous state from converting into more stable crystalline form. In preferred embodiments, ions known to act as inhibitors of crystalline hydroxyapatite formation may be added into the solution in trace amounts. These may be, for example, Mg ions in the form of less than 1.0 g $MgCl_2 \cdot 6H_2O$ (magnesium chloride), pyrophosphate ions in the form of less than 2 g $Na_4P_2O_7 \cdot 10H_2O$ (sodium pyrophosphate).

An infrared spectrum of the inert amorphous material at this point in the process is shown in FIG. 4(a). This spectrum contains peaks characteristic of P—O groups (600 and 1000 $cm^{-1}$), $CO_3^{2-}$ group (1,420–1,450 $cm^{-1}$) with relatively large peak of O—H group (~3,550 $cm^{-1}$). The inert amorphous material described above was then made into a reactive form by heating for 60 minutes at 450° C. (±3° C.). The IR of the heated material is shown in FIG. 4(b). This spectrum showed reduction of particular O—H and $CO_3^{2-}$ groups, indicating significant reduction of $H_2O$ and $CO_3^{2-}$ as $CO_2$ and $H_2O$. In similarly prepared samples the carbon content was observed to drop approximately 60% with a total carbonate ratio decreasing from 1.56% to 0.5%.

The overall morphological and ultrastructural properties of amorphous material is shown in FIG. 2, as seen under a transmission electron microscope. Note the "amorphous" appearance of the material with absence of sharp edges separating each granules with certain portion of the material to exhibit shapeless form (arrows). An extremely high specific surface area of 120 $m^2/g$, with an average pore size of approximately 130 Å was observed in this material.

EXAMPLE 2

This example describes the preparation of PCA calcium phosphate.

Dicalcium phosphate dihydrate was prepared at room temperature by the rapid addition of solution B (17.1 g $Ca(NO_3)_2 \cdot 4H_2O$ (calcium nitrate tetrahydrate); 250 ml distilled water; pH 5.5–6.) to a stirring solution A (10 g $H_9N_2O_4P$ (diammonium hydrogen phosphate); 500 ml distilled water; pH 7.8). Immediately thereafter, the sample was filtered using filter paper (0.05 sq. m) with medium filter speed and a vacuum pressure of about $10^{-2}$ torr. The material formed a thin cake which was washed with about 2 liters of distilled water and then dried at room temperature for 24–72 hrs.

Figure 11A:
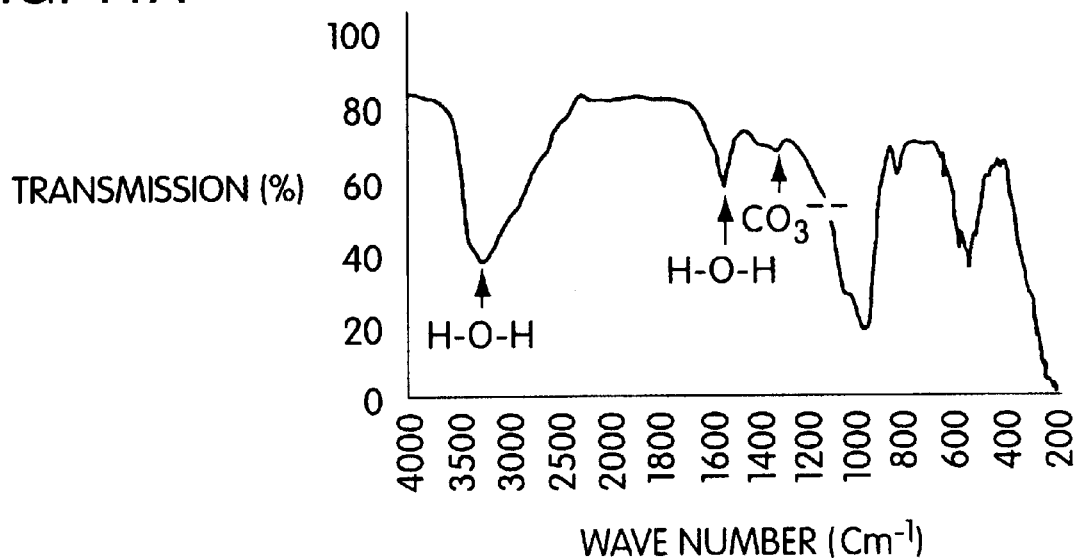
FIG. 11 shows infrared spectra of the reactive amorphous calcium phosphate of the present invention (a) prior to and (b) after heating step in which band intensities for the H-O-H group (~3,550 cm$^{-1}$ and 1,640 cm$^{-1}$) and $CO_3^{2-}$ group (1,420–1,450 cm$^{-1}$) are altered upon heat treatment.
Figure 11B:
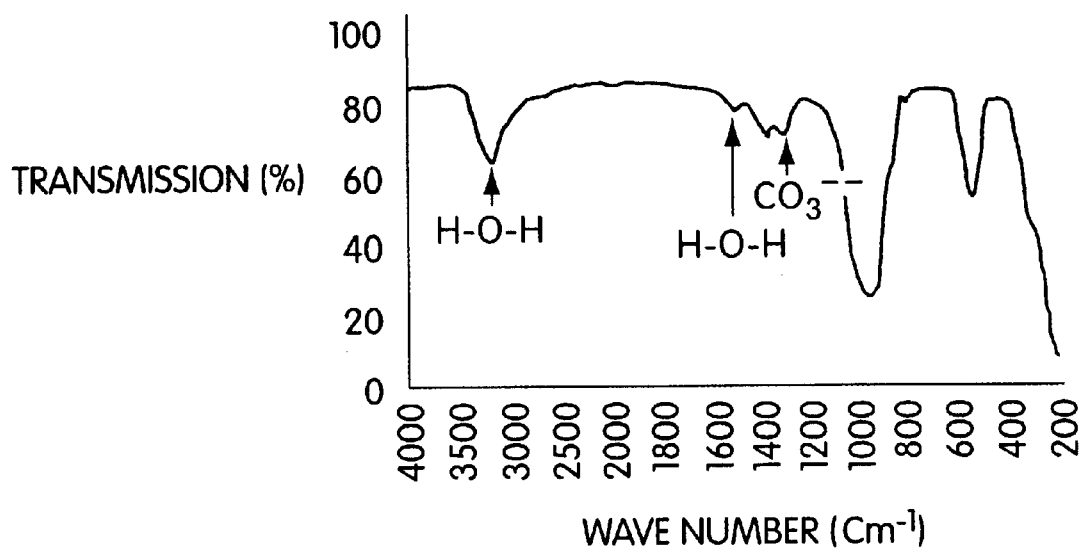
Figure 12:
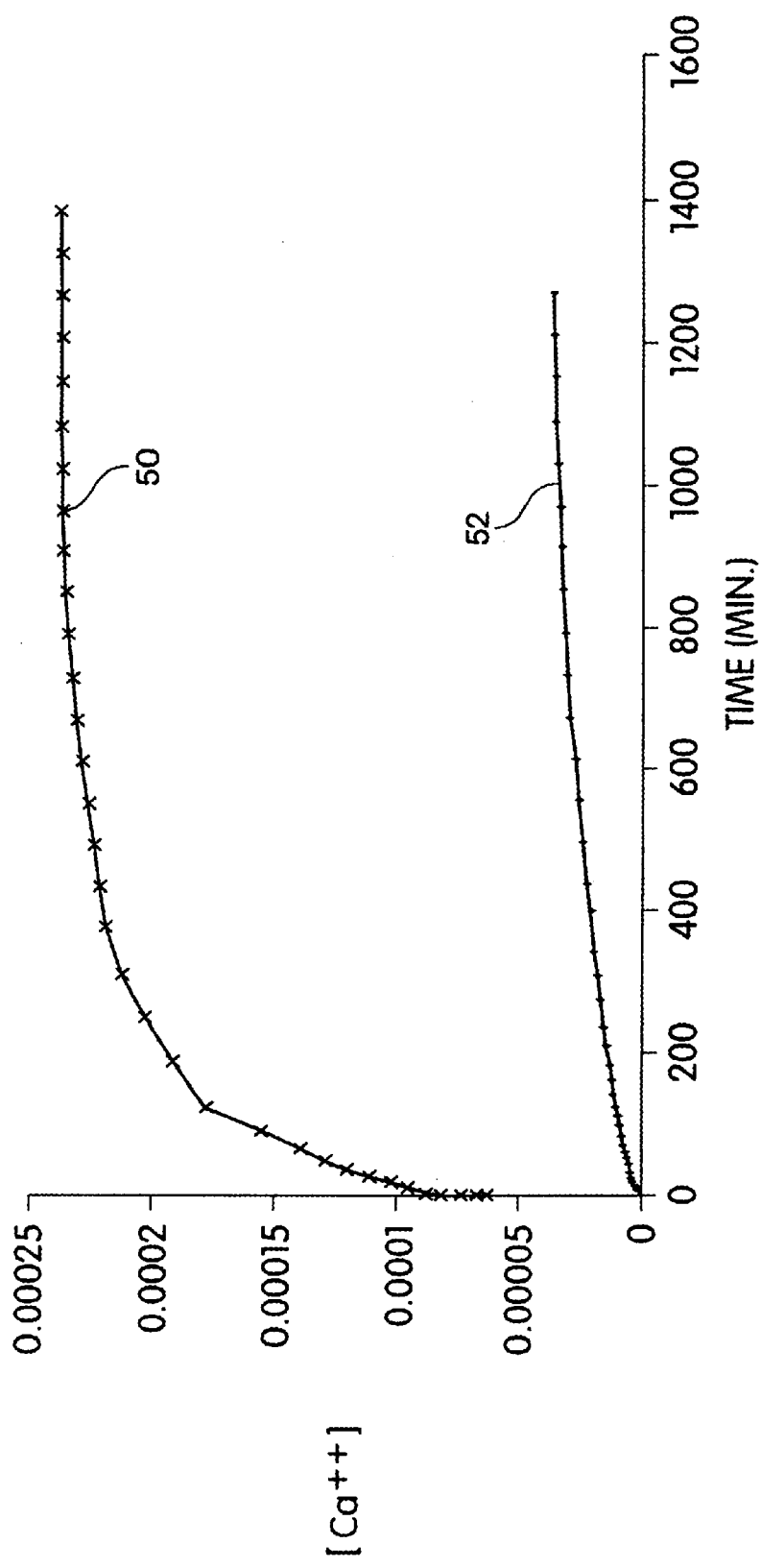
FIG. 12 is solubility curve of (a) a poorly crystalline apatitic calcium phosphate and (b) crystalline hydroxyapatite.

The reactive amorphous calcium phosphate material prepared from Example 1 was physically dry-mixed with dicalcium phosphate dihydrate ($CaHPO_4 \cdot 2H_2O$) at 50:50 wt % using a mortar and pestle for 3–5 min. Water (1 ml/g of mixed material) was then added to the powder mixture to yield a hydrated precursor of paste-like consistency. The amount of $H_2O$ added varied, depending on whether a thick or thin paste was desired. The paste material was then placed in a moist tissue environment where upon reaching body temperature (37° C.), hardened into a solid mass without exothermic behavior. The hardening process could be delayed for several hours by placing it into a refrigerating temperature of 4° C. The hardened material was composed of nanometer-sized, poorly crystalline hydroxyapatite with an inherent solubility property that exceeded reported solubilities for a synthetic hydroxyapatite material. This is demonstrated in FIG. 11, where the concentration of calcium ions released into a controlled pH buffer solution over 24 hrs at 37° C., was significantly higher for the PCA calcium phosphate material of the present invention (curve 50) than the standard crystalline hydroxyapatite material (curve 52).

EXAMPLE 3

This example demonstrates the preparation of PCA calcium phosphate material using materials having a selected particle size.

The reactive amorphous calcium phosphate material prepared as in Example 1, was physically dry-mixed with dicalcium phosphate dihydrate ($CaHPO_4 \cdot 2H_2O$) with a particle size of less than 100 $\mu$m at 50:50 wt. % using a SPEX 8510 laboratory mill for 2 min with a SPEX 8505 alumina ceramic grinding chamber, followed by sieving to a size of less than 100 $\mu$m. Water (1 ml/g of mixed material) was then added to the powder mixture to yield a paste-like consistency.

EXAMPLE 4

This example describes alternative methods for preparing a poorly crystalline apatitic calcium phosphate.

(a) Reactive ACP and DCPD were prepared as described in Examples 1 and 2. Water (0.8 ml) was added to ACP (0.5 g) and mixed thoroughly to homogeneity with a spatula to form a paste. 0.5 g of DCPD was then added to the paste and the paste was mixed for an approximated 2 min. The paste material was then placed in a moist tissue environment where upon reaching body temperature (37° C.), hardened into a solid mass without exothermic behavior.

(b) Reactive ACP and DCPD were prepared as described in Examples 1 and 2. Water (0.8 ml) was added to DCPD (0.5 g) and mixed thoroughly to homogeneity with a spatula to form a paste. 0.5 g of reactive ACP was then added to the paste and the paste was mixed for an additional 2 min. The paste material was then placed in a moist tissue environment where upon reaching body temperature (37° C.), hardened into a solid mass without exothermic behavior.

In both instances, the paste hardened after 30 minutes, indicating a successful reaction.

EXAMPLE 5

This example describes the preparation of PCA calcium phosphate using pre-hardened PCA calcium phosphate and crystalline hydroxyapatite as alternative second calcium phosphate sources. Both reacted with reactive amorphous ACP to produce a PCA calcium phosphate.

(a) Poorly crystalline HA is prepared as described in U.S. Ser. No. 08/554,817 filed May 19, 1995, incorporated herein by reference, using only carbonate as an inhibitor (no $Mg^{++}$ or pyrophosphate). The resultant powder was then lyophilized.

(b) Hydroxyapatite was obtained in powder form from Aldrich Chemicals (#28,939-6; lot 00325AQ).

Figure 13A:
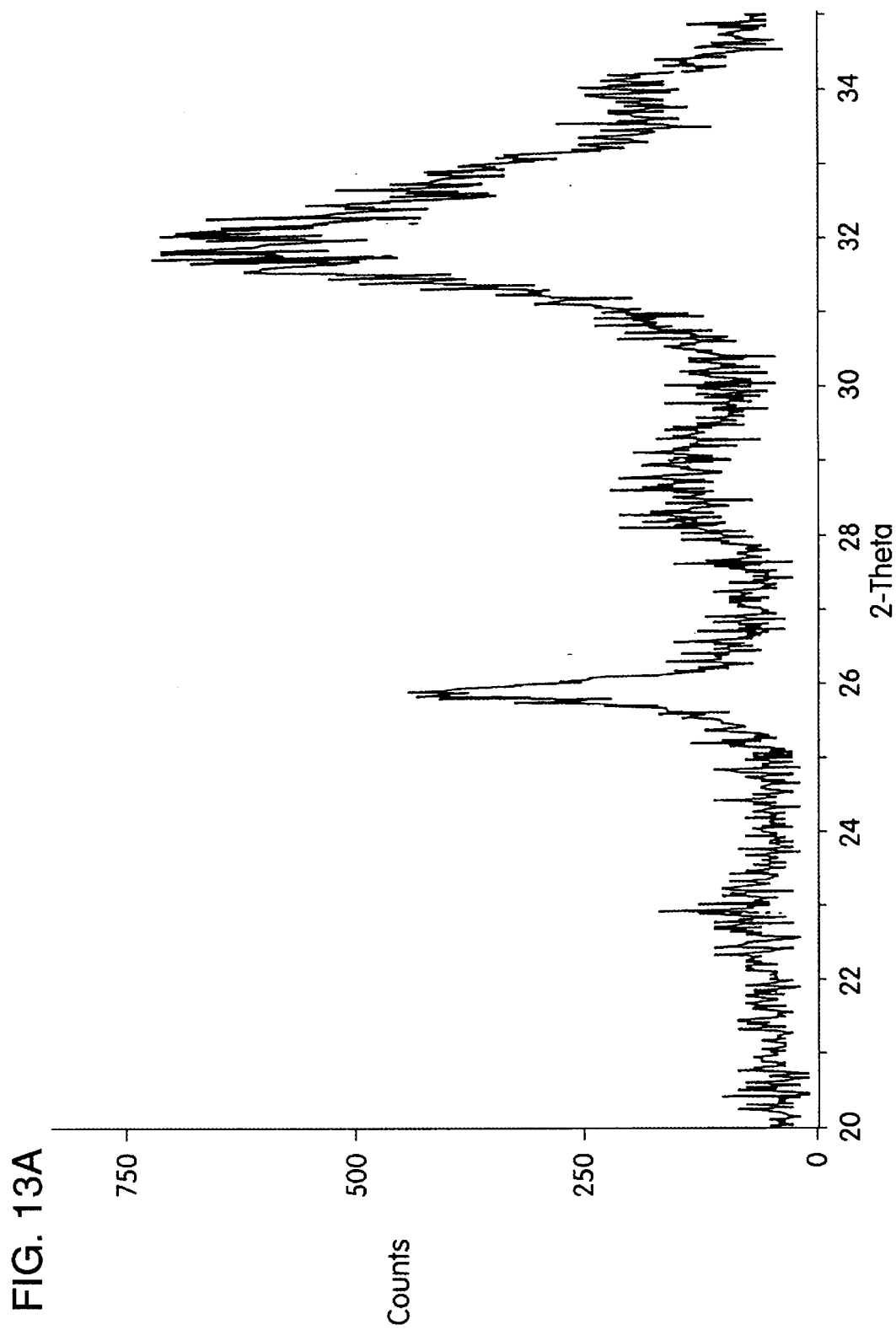
FIG. 13 is the X-ray diffraction pattern of a poorly crystalline apatitic calcium phosphate prepared using (a) a pre-hardened poorly crystalline apatitic calcium phosphate and (b) crystalline hydroxy apatite as the second calcium phosphate source.
Figure 13B:
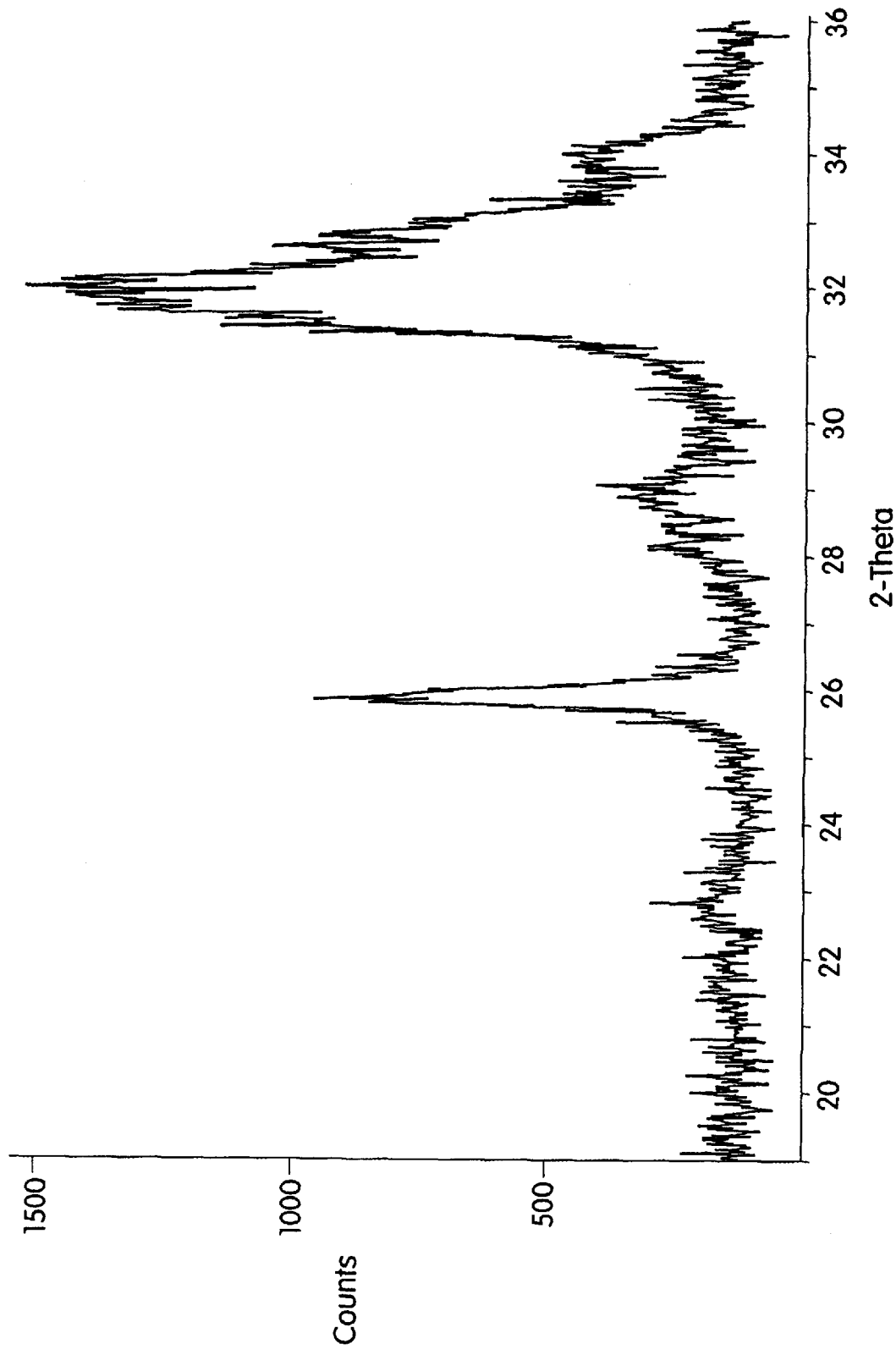

Each of the two powders was mixed 1:1 with reactive amorphous calcium phosphate, prepared as described in Example 1 and mixed with water. Both mixtures hardened within 30 minutes at 37° C. and IR spectra of the reaction products were substantially the same as that of the PCA calcium phosphate produced according to Example 2. XRD spectra are found in FIG. 13a and 13b, respectively.

EXAMPLE 6

This example describes the preparation of particulate PCA calcium phosphate of differing particle size which may be used in the composites of the invention.

Reactive amorphous calcium phosphate and DCPD are prepared as described in Examples 1 and 2 and are used to prepare poorly crystalline hydroxyapatite as described in Example 2. The hardened PCA calcium phosphate is lyophilized overnight and pulverized in a grinder and then passed through one or more sieves to obtain a desired particle size. Particles are then introduced into a PLGA. A variety of composite matrices may be prepared as follows:

(a) 25 μm average particle size PCA calcium phosphate (10% wt/wt) in PLGA;

(b) 25 μm average particle size PCA calcium phosphate (5% wt/wt) in PLGA;

(c) 100 μm average particle size PCA calcium phosphate (5% wt/wt) in PLGA; and (d) 200 μm average particle size PCA calcium phosphate (5% wt/wt) in PLGA.

The composites prepared as above are placed intramuscularly in a rodent and resorption rates determined according to Example 22 to identify composites suitable for use in resorbable bioceramic composites.

EXAMPLE 7

Characteristics of Injectable Paste for Formation of Synthetic PCA material from a Reactive, Amorphous Calcium Phosphate. These examples demonstrate the effect of fluid volume on the consistency and reactivity of injectable paste to be used in the formation of a synthetic, poorly crystalline hydroxyapatite material. Each of the pastes were prepared as described in Example 2, above, and the consistency and rate of reaction at room temperature and 37° C. were determined. Observations are reported in Table 1.

TABLE 1

Formability, injectability and reactivity of one gram PCA material prepared with variable water volume

| Example No. | water volume (mL) | formability | injectability | hardening time (min) (4° C./RT/37° C.) |
|---|---|---|---|---|
| 7-1 | 0.7 | – crumbles | – | –/–/– |
| 7-2 | 0.8* | +++ easily formed paste | + | >60/>60/30 |
| 7-3 | 0.9* | ++ toothpaste | ++ | >60/>60/30 |
| 7-4 | 1.0 | + liquid toothpaste | +++ | >60/>60/30 |

*Under some circumstances (e.g., evaporation) these samples may dry out somewhat over a period of one hour at room temperature. In such cases, additional water may be added to restore the original consistency.

EXAMPLE 8

This example demonstrates the preparation of PCA bioceramics using DCPDs of specific grain size distributions.

DCPD was prepared as described in example 2. The dry material was ground for 5 minutes in a SPEX 8510 laboratory mill with a SPEX 8505 alumina ceramic grinding chamber. Following grinding, the material was serially sieved through a Tyler test sieve shaker to produce DCPD with 8 different grain size distributions as indicated in Table 2.

TABLE 2

DCPD Grain Size Distribution

Figure 14:
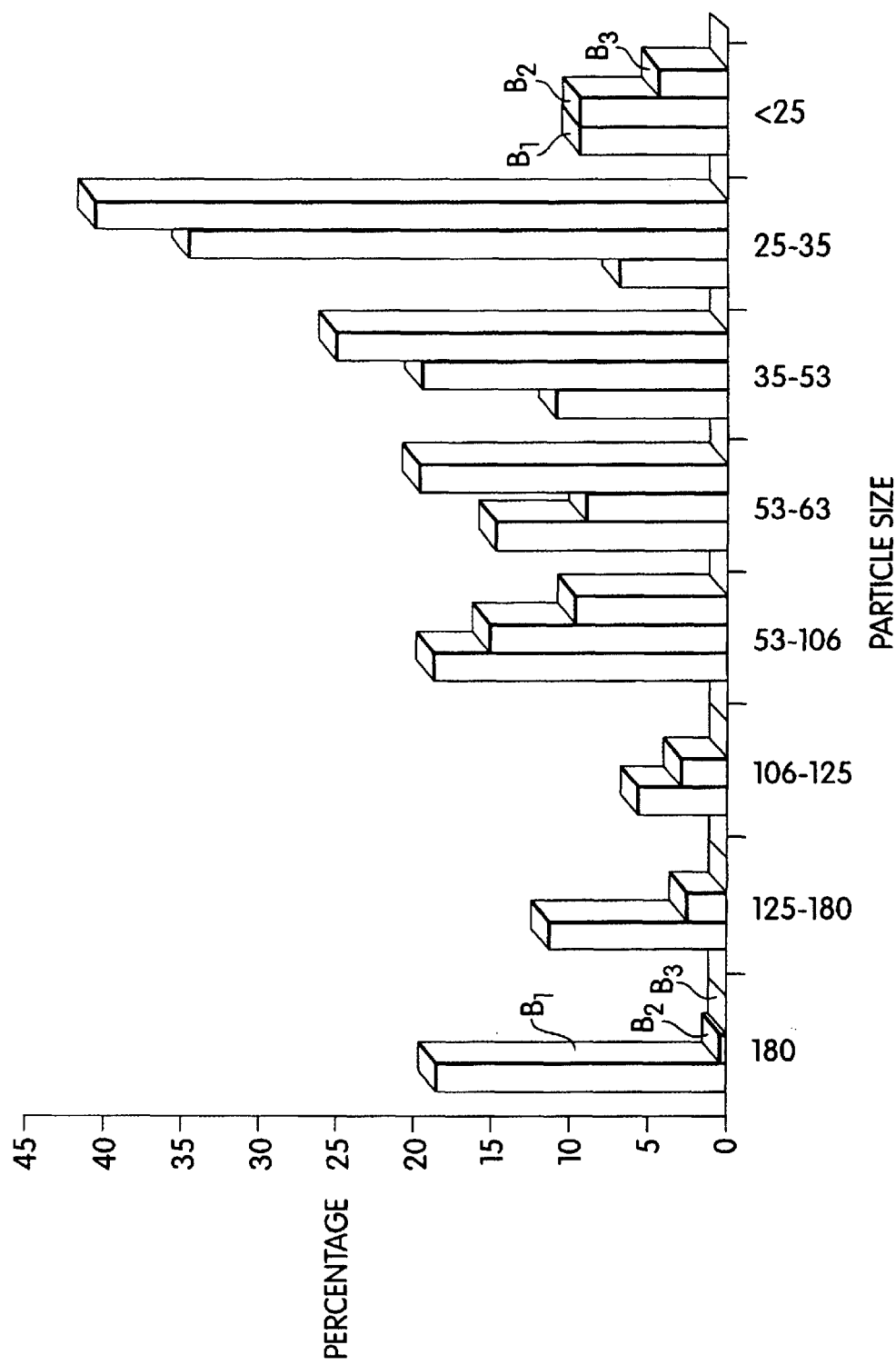
FIG. 14 is a bar graph displaying particle size v. percent of powder for various formulations described in Example 11.

| Sample | Grain Size Distribution |
|---|---|
| 1 | <25 mm |
| 2 | 25–35 mm |
| 3 | 35–53 mm |
| 4 | 53–63 mm |
| 5 | distribution B3 (Figure 14) |
| 6 | 106–125 mm |
| 7 | distribution B2 (Figure 14) |
| 8 | unsieved distribution B1 (Figure 14) |

It has been found that the preliminary grinding of DCPD prior to sieving can be replaced by a brief hand grinding using a mortar and pestle without substantially changing the results.

The reactive amorphous calcium phosphate material prepared from Example 1 was physically dry-mixed 1:1 (wt/wt) with one of the DCPD samples from Table 2 for 10 minutes using a SPEX 8510 laboratory mill with a SPEX 8505 alumina ceramic grinding chamber. Water (1.0–0.8 ml/gm of dry mix) was then added to the powder mixture to yield a hydrated PCA precursors with a paste-like consistency. Six of the eight samples indicated in Table 2 hardened well in 30 minutes at 37° C. Samples 6, 7 and 8 did not harden as quickly or as firmly as the other samples. Each of these samples had significantly higher percentages of >100 μm particles than the other samples. It is concluded from these observations that the use of smaller grain size DCPD leads to more rapid and complete hardening than larger grain size DCPD.

EXAMPLE 9

This example describes hardness testing of a PCA calcium phosphate and its composites.

PCA calcium phosphate was prepared according to Examples 1 and 2 to form a paste. The paste was placed into a 6×10 mm hollow Teflon® tube submersed in 37° C. water for 30 minutes. The hardened PCA calcium phosphate was then removed from the tube and placed in water at 37° C. for 1 hour and then, while still moist, placed vertically on an Instron 4206 having a dual load 10 Kg/15 ton load cell. Compressibility was determined using a crush test. Approximately, 200–250 N were required to bring the sample to failure. This force corresponds to a compressive strength of 7–9 MPa.

Poly(lactide) whiskers are prepared with average dimensions of about 5–100 μm diameter by 10–250 μm length. The whiskers are mixed with poorly crystalline hydroxyapatite paste prepared as described above at a concentration 10% wt/wt. The composite paste is hardened overnight at 37° C. in a moist environment. When tested for compressibility, the composite is found to have improved compressibility over the non-composite PCA calcium phosphate.

EXAMPLE 10

This example describes the preparation and testing of resorbable PCA calcium phosphate composites.

A PCA calcium phosphate/poly(lactide) composite paste is prepared as described in Example 6. The paste is packed into molds in the shape of intermedulary nails, support plates, and screws. The molds are heated to 37° C. for three hours in a moist environment and the hardened objects are removed from the mold. The composite objects are implanted into animal models according to the procedure set forth in Example 20, in all cases being sure to contact the object with bone forming cells. Composites which are found to be fully resorbed and ossified in less than 6 months are suitable for use as bioresorbable bioceramic composite implants.

EXAMPLE 11

This example describes a resorbable composite for use as a bone filler or cement. A PCA calcium phosphate/dextran composite may be prepared by first preparing the paste as described in Example 2. The paste may be well mixed with 10% vol/vol polydisperse dextran, hardened in a moist environment and shown to have improved strength and compressibility. The hardened composite may be then introduced into a fracture site in an animal model according to Example 20. The time for resorption and reossification are determined. Screening according to Example 21 is used to determine the suitability of the composite as a resorbable bioceramic implant.

EXAMPLE 12

This example describes the coating of PCA calcium phosphate particles with a biodegradable outer coating. Particles prepared in this way resorb and/or ossify with an initial delay period as compared to PCA calcium phosphate alone.

PCA calcium phosphate particles may be prepared as described in Example 2. The particles may be prepared in a series of homogeneous lots with average particle sizes in the range of 60–100 microns according to the method used in Example 3. These particles may be then uniformly dip coated with poly(lactide). The coated particles are placed intramuscularly in order to evaluate the resorption kinetics, which may be delayed as compared to uncoated particles.

EXAMPLE 13

This example describes the use of a PCA calcium phosphate/hydroxyapatite composite to produce new bone. This form of bone is useful in augmentation therapy.

Crystalline hydroxyapatite may be prepared or obtained as 50–200 micron particles. These particles may be introduced into a PCA calcium phosphate paste at approximately 1 to 50 wt % and may be well mixed. The resultant composite paste may be formed into the desired shape, seeded with bone forming cells and implanted adjacent to cortical bone and fixed by suturing and soft tissue approximation. The composite may also be seated on a recipient bone which has been surgically fashioned according to the method of Example 20. After three months, the implant site may be examined as in Example 20 to establish that the new bone impregnated with particulate hydroxyapatite is formed in the shape of the formed implant.

EXAMPLE 14

This example describes the formation of a PCA calcium phosphate composite with a lubricant.

A PCA calcium phosphate paste may be prepared according to Example 2. Silicone oil may be mixed with the paste at a concentration in the range of 0.1 to 30 wt %. Before the hardening reaction occurs, the paste may be injected through a 16–22 gauge needle and found to have significantly improved injectability as compared to an untreated paste.

EXAMPLE 15

This example demonstrates the use of a PCA calcium phosphate composite to embed an object in the recipient's bone. In addition to placement of anchoring devices, this approach can be used to embed almost any desired agent into a recipient's bone, including but not limited to support rods and fibers, imaging agents and friction reducing substances such as teflon plates.

A dacron loop approximately 1 mm in diameter may be formed on a 2 cm dacron suture. A knot may be placed within the suture approximately 2 mm from the loop. The suture may be then trimmed at the knot, leaving a loop with a 2 mm knotted tail. A 1 mm diameter hole may be drilled approximately 3 mm into a recipients's bone. The knotted end of the suture may be place within the hole and the hole may be then filled with PCA calcium phosphate paste. After six months, suture is evaluated for resorption in order to evaluate the composite's suitability as a resorbable bioceramic composite.

The procedure may be repeated in a second subject with the following modification. Following placement of the knotted suture within the hole, a prehardened PCA calcium phosphate plug may be wedged securely into the hole, thereby mechanically securing the suture in place. The hole may be then sealed with poorly crystalline hydroxyapatite paste. After six months, suture is evaluated for resorption in order to evaluate the composite's suitability as a resorbable bioceramic composite.

EXAMPLE 16

Implantation and Resorption of PCA calcium phosphate in a Bony Site. The purpose of this study was to assay resorption and ossification of PCA calcium phosphate in a bony implant site. The method is also useful for testing the resorption and ossification properties of PCA calcium phosphate formulations and composites of the invention.

The test article used was a PCA calcium phosphate formulation prepared as described in Example 2. The ACP and DCPD were mixed in the specified proportions and ground for 1 minute, 30 seconds in the SPEX grinder equipment.

Adult (>5 month old) NZW male rabbits were held in quarantine and acclimatized for a minimum of 10 days prior to the initiation of the study. Animals were individually housed in suspended stainless steel cages. Wood shavings were used in dropping pans under the cages. Prior to initiation of the study, animals were assigned to groups or treatments randomly and were identified by a numbered ear tattoo and by a corresponding cage card. All animals had single defects placed in one tibia. Timepoints for evaluations were 2, 4, and 8 weeks (2 animals at each timepoint). Surgery was performed under full anesthesia and aseptic surgical conditions.

After obtaining adequate anesthesia (e.g., ketamine/xylazine to effect), using aseptic technique, an incision was made over the lateral proximal tibia. The soft tissue was deflected away and the bone exposed. Using an approximately 5 mm trephine in a low speed dental handpiece with irrigation (0.9% physiologic saline) as needed, a ~5.5 mm diameter hole was cut through the cortical portion of the bone. The bony disk was dissected free from the cortex and the site was prepared for implantation. The hydrated precursor material in paste form was placed into the defect. Defects in control animals were left untreated. The soft tissues were then closed in layers. One sample per animal was prepared using this method.

Clinical observations of the animals' general health and well-being, with special regard to their ambulatory abilities, were made at least weekly. All animals appeared to be in good health. At the end of the study the animals were euthanized with an overdose of anesthetic and the implant site collected. Radiographs of the tibiae were made at scheduled intervals including after surgery and at the time of necropsy.

The implantation sites were fixed in formalin and stained with either hematoxylin and eosin, Masson's trichrome, or Von Kossa stained slides from decalcified samples. Undecalcified histological samples were also prepared and stained with light green basic fuschin. Slides were microscopically evaluated by a board certified veterinary pathologist (ACVP) with experience in laboratory animal pathology. Subjective observations were made of bone morphology, and presence or absence of organized bone and of detectable PCA calcium phosphate material was noted.

Figure 15A:
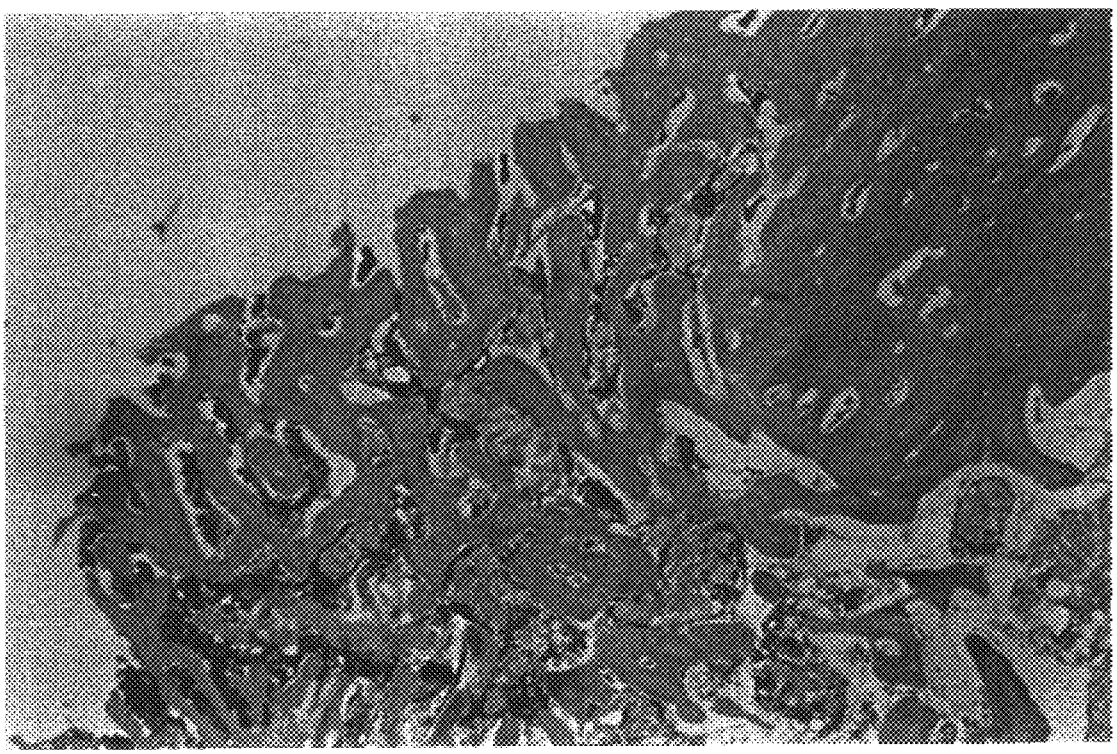
in FIG. 15a, the small arrows indicate one edge of the defect; the large arrowhead is it the yet unbridged defect, in FIG. 15b, large arrowheads denote one edge of the defect, and in both figures, magnification is 4×, bone is decalcified, and slides are treated with hematoxylin and eosin.
Figure 15B:
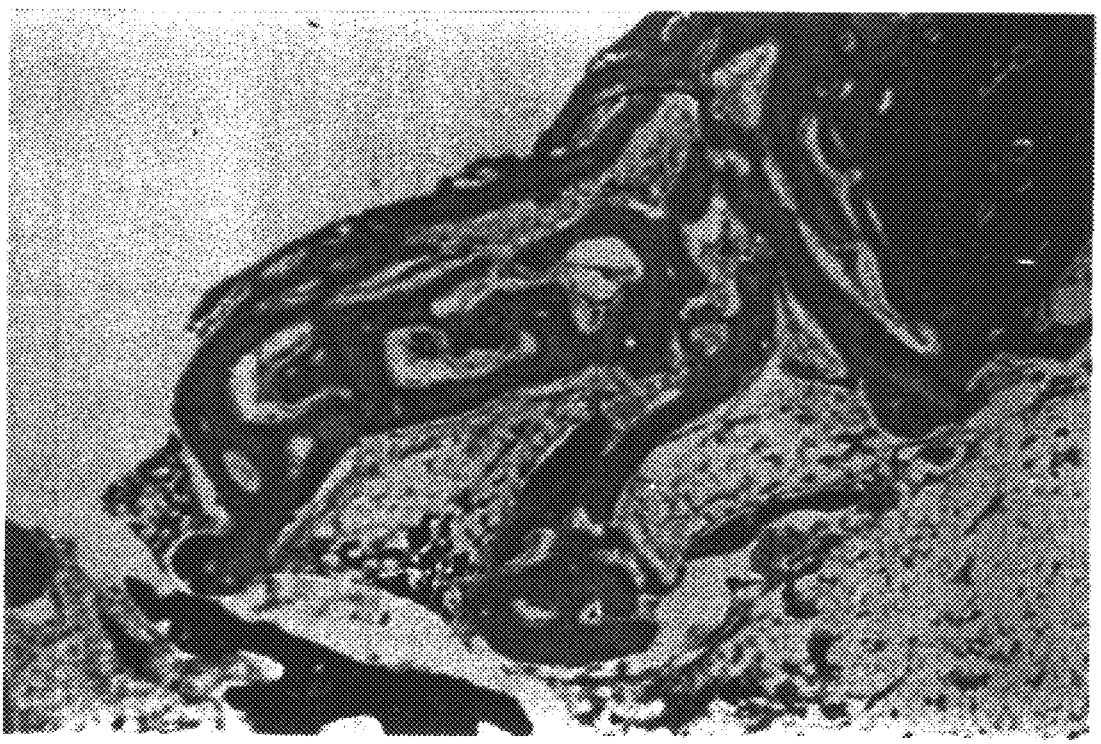
FIG. 15 presents photomicrographs of tibial defects either untreated (15a) or treated (15a) with a PCA calcium phosphate of the present invention.

Histological results indicated some mineralization at 2 weeks. By 4–6 weeks, animals receiving implants had normal trabecular bone at the implant site with no evidence of remaining PCA calcium phosphate. The untreated controls had not fully healed in that they had less than full ingrowth and/or had non-cortical-type bone. FIGS. 15 and 15a are photomicrographs of untreated and treated tibia defects, respectively, 2 weeks after surgery. As can be seen, bone to the right of the defect edge in the untreated sample (FIG. 15 is thin trabecular bone; new bone to the right of the defect edge in the treated sample is thick trabecular bone.

EXAMPLE 17

Implantation and Resorption of PCA calcium phosphate in a Subcutaneous Site. This example demonstrates the resorption of the inventive PCA calcium phosphate when implanted subcutaneously into rats. It also demonstrates a useful screening procedure to test resorption characteristics of new formulations of bioceramic implant materials and composites.

Eighty male and eighty female Sprague-Dawley rats were each implanted with 4 ml (2–4 gm) of the inventive PCA (prepared according to Example 4) into the dorsal subcutis (>10× the amount considered maximal in humans on a per kg basis). Control animals were treated with an equal volume of saline. Operation procedures are described in Example 18. The rats were sacrificed according to the schedule presented below in Table 3; the implant site was examined as described in Example 17

TABLE 3

| Sacrifice Schedule | |
|---|---|
| Sacrifice Timepoint | PCA calcium phosphate implant |
| 1 week | 5 m/5 f |
| 2 weeks | 5 m/5 f |
| 1 month | 5 m/5 f |
| 3 months | 5 m/5 f 1 year |
| 20 m/20 f | |

Blood for clinical pathology analyses was collected via retroorbital sinus or cardiac puncture (all by the same method) while the animals were under $CO_2$ anesthesia. Blood samples were collected from each group of animals prior to scheduled sacrifice. Clinical observations of the animals for general health and well-being were performed at least weekly until 3 months, and then monthly.

At 1 week PCA material was present at the implant site and was found associated with moderate to marked granulomas presumable associated with the resorption process. At week two a small amount of PCA material was still present at the implant site and associated granulomas were mild to moderate. By week four most tissue appeared normal with a few mild granulomas persisting at the implant site. At week twelve no evidence of the implant remained.

EXAMPLE 18

Implantation and Resorption of PCA calcium phosphate in an Intramuscular Site. This example describes the preparation of PCA material that have varied in vivo resorption times as a result of varied grinding times. Individual dry precursors, ACP and DCPD were prepared as described in Example 4. Several different formulations of DCPD and ACP were then prepared by i) grinding DCPD for 15 sec, 30 sec, 1 min, 2.5 min, or 5 min in a SPEX grinder; ii) combining the ground DCPD 1:1 with ACP; and iii) grinding the mixture for an additional 15 sec, 30 sec, 1 min, 2.5 min, or 5 min, respectively. Total grinding times for the different preparations were therefore 30 sec, 1 min, 2 min ("type 2" powders), 5 min, and 10 min ("type 10" powders).

The PCA calcium phosphate, sterilized in powder form by approximately 2.5 Mrad of gamma irradiation, was prepared as described in Example 2 by taking the material in powder form and mixing with sterile water or saline and forming it into approximately 1 cm disks 2 mm thick and incubated for a minimum of 30 minutes at 37° C. Disks were implanted into adult male New Zealand White Rabbits immediately following fabrication.

Animals were assigned to dose groups which contained 3 males for a total of 15 animals. The implants were assigned to the rabbits randomly. 10–15 minutes prior to the surgery, the animal was premedicated with xylazine (10 mg/kg, i.m.). The animal was then given ketamine (50 mg/kg, i.m.). The dorsal surface of the animal was clipped free of hair and washed with a betadine surgical solution and alcohol. Before the surgery the animal was monitored to be sure that is was properly anesthetized. To do this, pressure was applied to the foot pad. When there was no response, the animal was properly anesthetized. Throughout the procedure, the animal was monitored for whisker twitching and the toe-pinch reflect, which indicated that the animal was not waking up.

Using aseptic technique and a scalpel blade, an incision 1–2 cm in length was made in the skin over the m. longissimus lumborum (which lies along both sides of the spine). When the incision was made, the underlying fascia and muscle was also cut to allow the sample to pas into the muscle. The sample disk was placed directly into the muscle, being sure that the entire implant was embedded in the muscle. The muscle was closed with a single absorbable suture and the skin was stitched closed subcutaneously. Metal skin staples were used to close the external skin surface incision. Five samples were placed on each side in this manner. Each sample was placed at the end of the incision and they were approximately 1 cm apart from each other (see diagram). The samples were in the form of 7 mm by 2 mm disks weighing approximately 150 mg. The animals were monitored and were given buprenorphine (0.02–0.05 mg/kg, s.q) upon awakening. The analgesic was administered 2 times per day for three days after surgery.

The animals were radiographed immediately after the surgery and for every two weeks thereafter. The radiographs were compared to track the resorption of the materials. A standardized method was used for the radiographs to minimize any variation between timepoints.

After euthanasia, implant sites were first evaluated by gross examination. In those sites with visible implants, the implants appeared as grey to yellow solid discs. In those sites where the implant had been resorbed, areas of red to tan discoloration of the muscle were observed.

Muscle tissue, with the implants, was removed, being careful not to disturb the implants. The tissues and the identifying marks were placed into labeled jars filled with 10% neutral buffered formalin. All implant sites were processed and evaluated microscopically. Observations included focal fibrosis, focal granulomatous inflammation, and appearance of the implant (in some cases). Fibrosis was primarily seen as fibrocytes and collagen. Animals with gross resorption had fibrosis and minimal to moderate granulomatous focal inflammation. Granulomatous inflammation was seen as focal aggregates of macrophages and giant cells, often with intracytoplasmic crystals, and occasional heterophils and lymphocytes. Inflammation around the non-resorbed implants was primarily minimal to mild fibrosis and/or granulomatous inflammation, both of which are within the acceptable range for intramuscular implants.

At four weeks, the pellets made from PCA calcium phosphate implants that had been prepared by grinding for 30 seconds, 1 minute, or 2 minutes were fully resorbed. Those that had been prepared by grinding for 5 minutes or 10 minutes were not fully resorbed.

EXAMPLE 19

Implantation and Resorption of PCA calcium phosphate in a Bony Site. The purpose of this study was to assay resorption and ossification of the PCA calcium phosphate of the invention in a bony site.

Mature (>1 year) beagle dogs were employed for this study because of their size and historical use as a model for bone studies. The tibia of the dog is large enough to allow large (>5 mm) defects to be created and studied without compressing the ability of the animal to ambulate without inducing fractures secondary to induction of defects in the bones.

Ten adult male and female beagle dogs (6.0–15.0 kg) received the same treatment; Defects were created in the lateral surface of the tibial crest cortex (8 mm or 10 mm) in each tibiae. PCA calcium phosphate was placed in the defect in one tibia and the other tibia served as a control.

An incision was made over the proximal tibia. The soft tissue was deflected away and the bone was exposed. Using an 8 mm trephine in a low speed dental handpiece with irrigation (0.9% physiologic saline) as needed, the bony disk was dissected free and the site was prepared for implantation. The inventive calcium phosphate material (solid or paste) was placed into the defect. The soft tissues were then closed in layers. One to three samples per animal were performed using this method. The animals were allowed to heal for scheduled periods of time.

Animals were assessed by clinical observations, radiographs, and microscopy of the defect sites at 0, 2, 4, and 8 weeks. Specifically, tibia radiographs were taken every 2 weeks throughout the study. The radiographs were used to determine the duration of the study. Approximately at the end of every 2 weeks, 2 animals were sacrificed and the test sites were removed for histology. The implantation sites were prepared as undecalcified and decalcified sections.

Two dogs were used as pilot animals and did not receive and PCA material. In these pilot animals, some healing was observed radiographically at 2 weeks. By 6–8 weeks, the defect was completely healed. The size of dog defects was determined to be optimal at 1 cm. In the remaining 8 dogs, control defects healed within 6 weeks; treated defects healed in 2 to 4 weeks. The quality of the bone in the control defects was thin trabecular bone; in the treated defects, the bone was thick trabecular to cortical type bone. Thus, the treated defects healed approximately 2 weeks faster than did untreated defects, and healed with better bone thickness.

Figure 16:
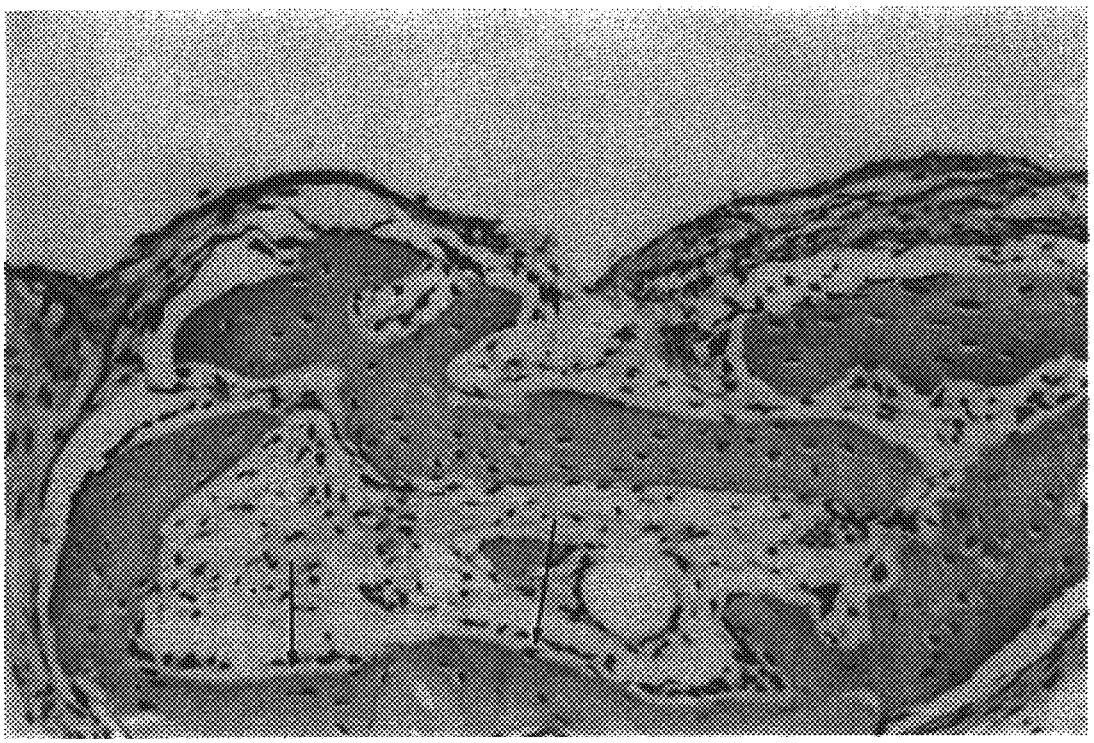
FIG. 16 is a photomicrograph of canine trabecular bone grown into a defect treated with the PCA calcium phosphate of the present invention 8 weeks after surgery (magnification 10×; decalcified; hematoxylin and eosin)

FIG. 16 shows a highly magnified (10×) photograph of canine trabecular bone growth into a defect site treated with the PCA material of the invention 8 weeks after surgery. The small arrows denote osteoblast—like cells lining the bone spicules and are indicative of enhanced cellular activity.

Figure 17:
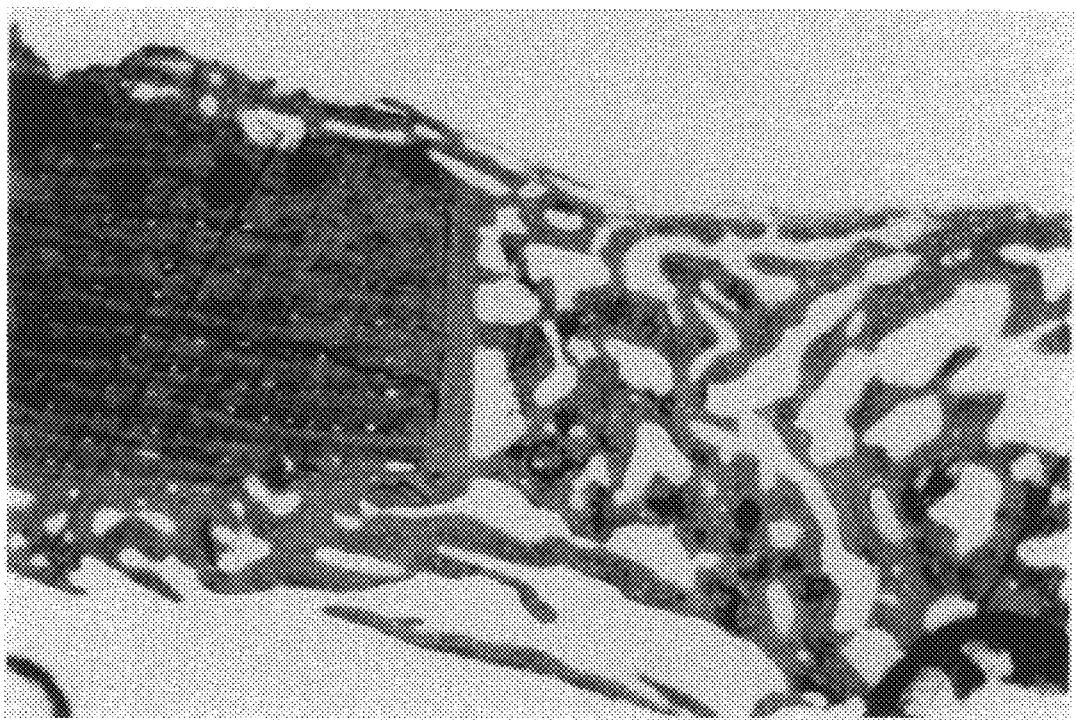
FIG. 17 is a photomicrograph of a canine cortical bone defect that was treated with the PCA calcium phosphate of the present invention 4 weeks after surgery (magnification 4×; undecalcified, Light Green Basic Fuchsin)

FIG. 17 shows a photomicrograph of a canine cortical bone defect treated with the PCA material of the invention. The large arrows indicate one edge of the defect. The new bone growth is to the right of the defect; at 4 weeks after surgery, this growth is thick trabecular bone.

EXAMPLE 20

Implantation and Resorption of PCA calcium phosphate in a Bony Site. The purpose of this study was to assay resorption and ossification of the PCA calcium phosphate of the invention, and to establish parameters for screening test PCA calcium phosphate materials.

Eighteen adult (>3 month old) NZW male rabbits were used in these studies. After obtaining adequate anesthesia (e.g., ketamine/xylazine to effect), using aseptic technique, an incision was made over the proximal tibia. The soft tissue was deflected away and the bone was exposed. Using an approximately 5 mm trephine in a low speed dental handpiece with irrigation (0.9% physiologic saline) as needed, the bony disk was dissected free and the site was prepared for implantation. The inventive PCA calcium phosphate material (solid, granules or paste) was placed into the defect. The soft tissues were then closed in layers.

Clinical observations of the animals general health and well-being, with special regard to ambulation, were performed weekly and in more detail at the time of the bi-weekly radiographs. Radiographs of the tibiae were made at scheduled intervals including after surgery and at the time of necropsy.

The implantation sites were prepared as hematoxylin & eosin, Masson's trichrome decalcified samples and as undecalcified slides.

Findings and clinical observations were associated with surgery and were not associated with the PCA calcium phosphate implants. Postsurgical clinical observations were within the range of anticipated findings for surgery-related trauma. Radiographs were taken immediately postsurgery and at each scheduled sacrifice timepoint.

Immediately after surgery, all bone defect sites were distinct; implants appeared to have the same radiodensity as bone. At 2 weeks postsurgery, control defects had distinct sites and implant sites were less distinct and blended into surrounding bone; similar findings were observed at 4 weeks. At 7 weeks, all sites appeared similar with increased radiodensity. Grossly, defect sites at 2 weeks were visible clearly in control and treated animals. At 4 weeks and greater, the implant or control sites could not be grossly ascertained.

Radiographic findings indicated little change in the control animals until week 7; animals treated with inventive PCA material had increasing radiodensity in the defect over time. Defects in control animals had some new bone ingrowth, predominantly of the thin trabecular type, within 4–7 weeks. Defects in treated animals had bone ingrowth as early as 2 weeks and by 7 weeks were filled with new bone. Microscopic findings are consistent with enhanced bone replacement with PCA calcium phosphate implants. Taken together, this study shows that 5 mm defects in rabbit tibia heal or have new bone growth in control animals by 7 weeks and in animals treated with the inventive PCA material by 4 weeks. Also, this rabbit unicortical 5 mm critical sized defect model is useful to analyze test articles for there resorptive and ossificative properties.

Figure 18A:
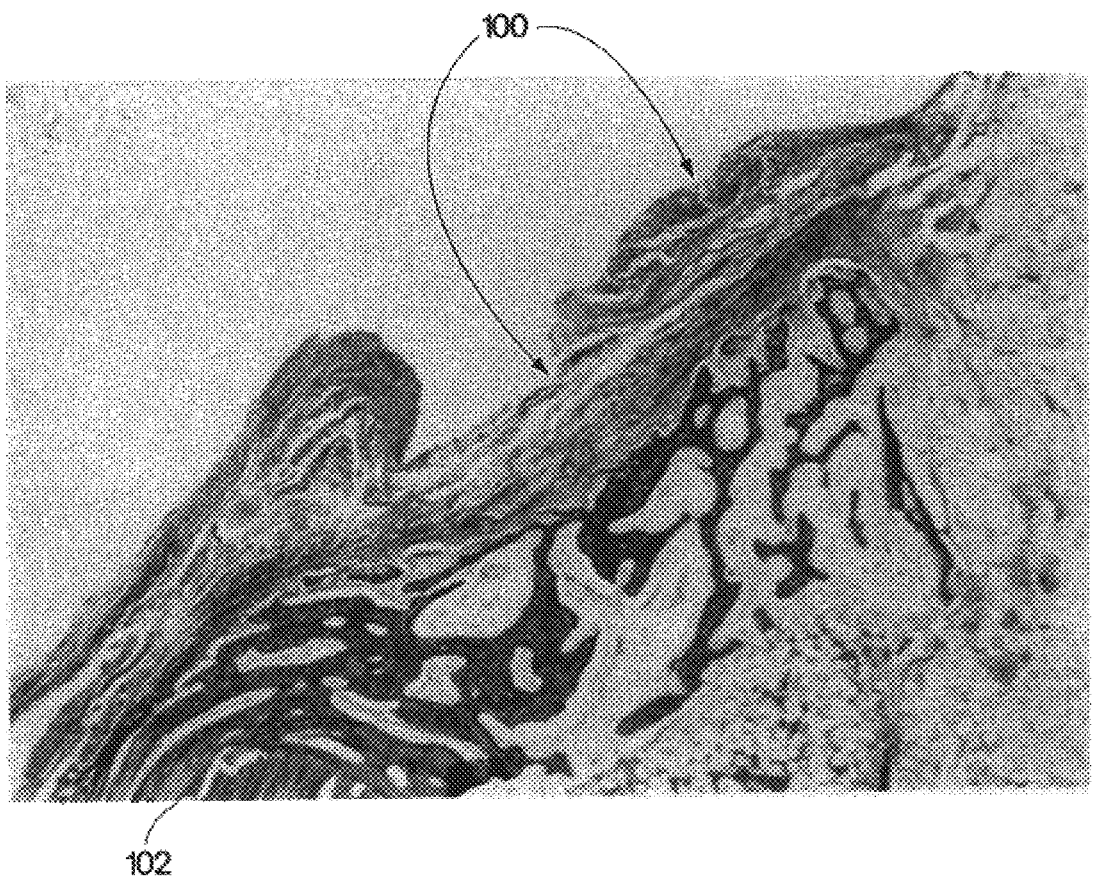
FIG. 18 presents photomicrographs of untreated (FIG. 18a) and treated (FIG. 18b rabbit tibia defects 4 weeks after surgery (magnification 4×; decalcified; Masson's Trichrome)
Figure 18B:
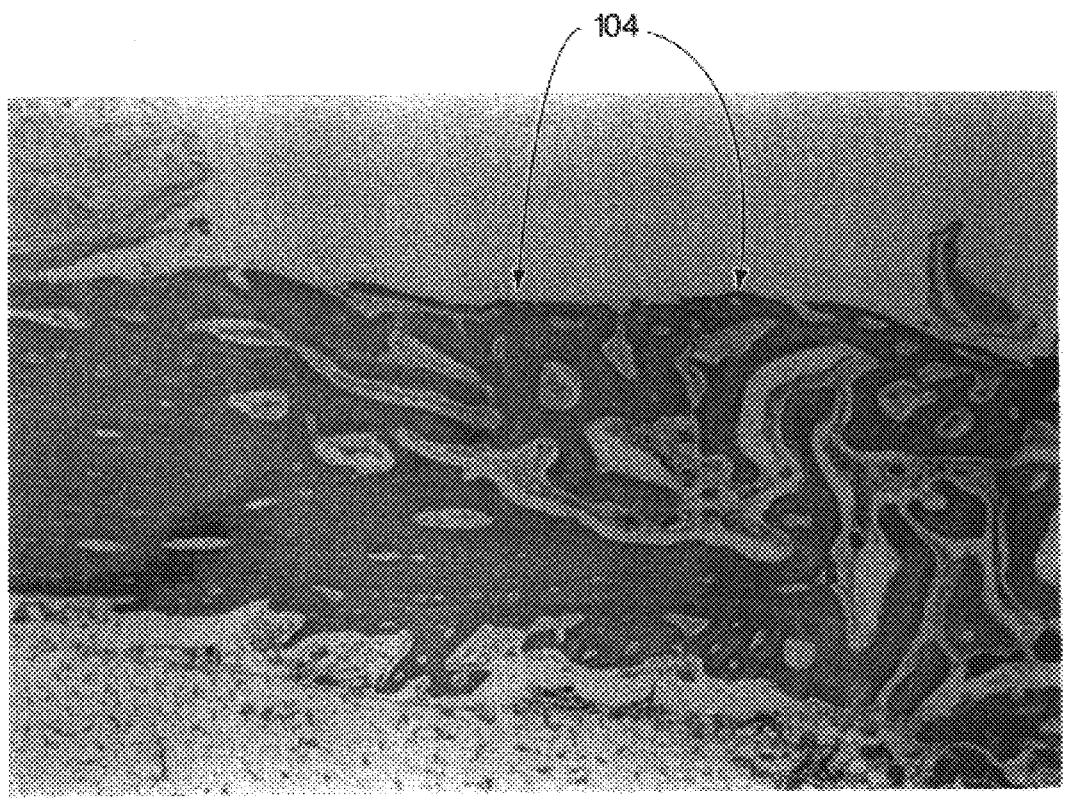

FIG. 18 shows photomicrographs of untreated (FIG. 18a) and treated (18b) rabbit tibia defects 4 weeks after surgery. The large arrow indicates the edge of the defect. In FIG. 18a, small arrows 100 denote an abundance of fibrous connective tissue on the defect site. The large arrowhead 102 points to new trabecular bone in the defect. In FIG. 18b, the two small arrows 104 demarcate the thick trabecular bone growth in the defect site.

EXAMPLE 21

This example demonstrates the efficacy of the inventive PCA calcium phosphate in promoting the healing in a large animal model, of a full segmental defect in a weight bearing limb.

Hydrated precursors Type 2 and Type 10 were prepared and treated immediately prior to surgery as described in Example 18.

Animals fasted for 24 hours prior to anesthesia, during this time interval water was available ad libitum. Ketamin (Aescoket®, 10 mg/kg i.m.) and atropine (1.5 mg i.m.) was administered as a pre-medication about 15 minutes before fully anesthetizing the animals. Etomidate (Hypnomidaat®, 0.3 mg/kg i.v.) was used as the anesthetic. After intubation, anesthesia was maintained with an $O_2/N_2O$-mixture (1:1, vol/vol) supplemented with 2% isoflurane.

Surgery was performed asceptically under full anesthesia. After shaving and iodinating the skin, an incision was made over the anteromedial side of the tibia. The muscles were bluntly dissected and the tibial shaft was prepared free of tissue to as great an extent as possible. After reaming the medullary cavity, an intramedullary nail (diameter 8 mm) was inserted via a hole in the anterior tibial plateau. The inserted nail was locked with two proximal and two distal bolts. A 20 mm osteoperiostal segmental defect was then created in the mid-shaft of the tibia with the aid of a thread saw and an oscillating saw.

The defect was filled according to the treatment group. In one group, autologous bone was harvested from the ipsilateral iliac crest and placed into the defect. In the other group, approximately 2–4 g of the hydrated PCA calcium phosphate precursor (type 2 or type 10) was applied by hand to fill the defect. The soft tissues and the skin were closed in layers with resorbable suture material.

The animals received post operative lincomycin/spectinomycin (Vualin Plus®, 5 mg/10 mg per kg per day) for 3 days by intramuscular injection. The animals were kept outside in the meadow as soon as full weight bearing of the operated limb was possible. Animals were sacrificed prior to explanation of the tibiae as follows: As a premedication ketamin (Aescoket®, 500 mg i.m.) and xylazin (Rompun®, 40 mg i.m.) were given. Then 0.5 mg fentanylcitrate (Fentanyl®), 10 mg etomidate (Hypnomidate®), 4 mg pancuronium bromide (Pavulon®), and 1.4 gram potassium chloride were administered intravenously.

Animals receiving the inventive PCA calcium phosphate demonstrated complete healing at three months. The test bones were then dissected from the animal and tested for strength. Preliminary results indicated that the inventive PCA calcium phosphate was resorbed and ossified to produce bone equal to or better than autologous implants in less than three months.

EXAMPLE 22

The purpose of this study was to evaluate resorption, ossification and biocompatibility of two formulations of the inventive PCA calcium phosphate in canine mandibular sites. Prehardened PCA calcium phosphate was implanted in a canine mandibular onlay model which additionally may be used as an augmentation model.

The test article was PCA calcium phosphate in two formulations, corresponding to Types 2 and 10 described in Example 18. The PCA calcium phosphate was pre-hardened in a moist environment at approx. 40° C. immediately prior to implantation. The control implants were 3 mm×4 mm cylinders of silicone and porous hydroxyapatite, respectively.

Two adult female hound-type dogs (20 to 25 kg) were used in the study. Both dogs received two control implants (1 of each) on the right side of the mandible and one each of the Type 2 and Type 10 PCA calcium phosphate formulations on the left (opposite) side.

Implantation was performed under full anesthesia and aseptic surgical conditions. The animals were premedicated with tranquilizers and atropine-type agents and induced with barbiturates. The animal's vital signs (temperature, heart rate, respiratory rate) were monitored before and throughout the procedure. The animals were tested for proper anesthetic depth by toe pinch and corneal stimulus. After obtaining adequate anesthesia, using aseptic technique, an incision was made in the skin over the midlateral ventral surface of the mandible and proximal neck (over the mandible lower edge). The soft tissue was deflected away and the bone was exposed. The periosteum over the outer mandibular surface was elevated and the bone surface was roughened with a burr or drill until it was rough and bloody in a shape to accept the cylindrical implants. The control articles and pre-hardened PCA calcium phosphate were placed into the defects. Two samples per animal per side were onlaid onto each outer mandible surface using this method (two experimental PCA calcium phosphate samples and two controls). The samples were placed about 1 cm to insure that they do not appose each other. The periosteum was closed first using 3.0 vicryl. The soft tissues were then closed in layers with 3-0 vicryl absorbable suture. The skin was closed with simple interrupted sutures of 5-0 nylon. The animals were allowed to heal for scheduled periods of time. One dog was sacrificed at 3 weeks and the other at 3 months and the test sites were removed for histology. All animals were euthanized and identifying marks were collected.

The implantation sites were prepared as undecalcified sections. Sections were evaluated for biointegration, biodegradation, and biocompatibility.

The results were as follows: At all time points excellent biocompatibility was observed. No giant cells and minimal macrophage were observed. There was only minimal reaction layer of only a few cells thickness at the base of the PCA calcium phosphate implants. This is significantly better than was observed for either of the controls.

At three weeks, the majority of the Type 2 material was resorbed. At twelve weeks, the Type 2 was completely resorbed to the surface of the original bone. Additionally the bone in the socket was not fully differentiated.

The Type 10 samples demonstrated osseointegration with new bone ingrowth and cell migration into the implant. The implant itself was approximately 10% resorbed after twelve weeks.

The silicon control implant, which is not resorbable, displayed a mild to moderate foreign body reaction. Voids were unfilled at three weeks, but by twelve weeks were filled with fibrous tissue. The hydroxyapatite control implant showed no signs of resorption or osseointegration within the first twelve weeks.

This experiment confirms the excellent biocompatibility of the inventive PCA calcium phosphate. Additionally, a difference in resorption time between the two PCA formulations was observed, with a prolonged resorption time course for the sample in which the precursors were mixed/ground for a longer period of time (Type B).

The results also point out the slower resorption and ossification properties observed in the non-load bearing mandible implant site as compared to the rapidly ossifying load bearing applications of Example 21. Finally, the results demonstrate the need for slowly resorbing PCAs for proper osseointegration in augmentation plastic surgery.

EXAMPLE 23

Efficacy Study of PCA in the Canine Alveolar Augmentation/Tooth Socket Model. This example demonstrates the use of the inventive PCA to restore bone tissue in an extracted canine tooth pocket.

The animals are premedicated with tranquilizers and atropine-type agents and induced and maintained with barbiturates. The animal's vital signs (temperature, heart rate, respiratory rate) are monitored before and throughout the procedure. The animal is then tested for proper anesthetic depth by toe pinch and corneal stimulus.

After obtaining adequate anesthesia, the gingival soft tissue is gently deflected away form the periphery of each premolar. The premolars are drilled in half with a slow speed dental drill and saline irrigation from the oral surface of the tooth to the lower surface between the roots. Each tooth half is then firmly grasped with extraction forceps and gently but firmly rotated until the tooth attachments are broken. The halves of each tooth are then removed. Bleeding is stopped by pressure and time. All premolars are extracted as described. After tooth removal and before PCA calcium phosphate placement, the lingual to buccal alveolar thickness is measured and recorded in at least 3 locations; these measurements are repeated after PCA calcium phosphate placement and at the time of necropsy and are used as a measure of bone ingrowth.

PCA calcium phosphate is prepared as Type 10 as described in Example 18. The empty tooth sockets/alveoli are located along one side of the mandible in the spaces formerly occupied by the premolar teeth. All dogs are implanted with PCA calcium phosphate in one side of the mandible and the opposite side remain untreated as unfilled controls. The gingival soft tissues are then closed in layers with 3-0 suture. After the surgical procedure the animals are monitored until they are stable.

The animals are allowed to heal for scheduled periods of time. Two dogs are sacrificed at 3 weeks, and two dogs are sacrificed at 2 months.

All animals are euthanized with a commercially prepared product used for euthanasia (such as sodium pentobarbital), and the mandibles and identifying marks are then collected and preserved in 10% neutral buffered formalin or another suitable fixative for decalcified and undecalcified bone sections. Mandibles are measured as described above and radiographed. The test sites thereafter are removed for histology.

The implantation sites are prepared as decalcified and undecalcified sections. Sections are evaluated for biointegration, biodegradation, and biocompatibility.

Figure 19:
FIG. 19 is a photomicrograph of a canine tooth socket defect that was treated with the PCA calcium phosphate of the present invention (magnification 4×; undecalcified, Light Green Basic Fuchsin)

A similar procedure was performed on a single dog. The implant was shown to bioresorb and to exhibit osseointegration within four weeks. FIG. 19 is a photograph of a histological slide of the tooth socket implant site four weeks after surgery demonstrating the extent of bone ingrowth into the socket. The large arrows indicate the boarder between the natural bone 1 and implant site 2. Note the extensive ingrowth of bone tissue at site 2. The gingival tissue is indicated at 3.

EXAMPLE 24

Osteoporotic Spinal Chord. This example demonstrates the procedure used for the treatment of osteoporatic vertebra.

Figure 20:
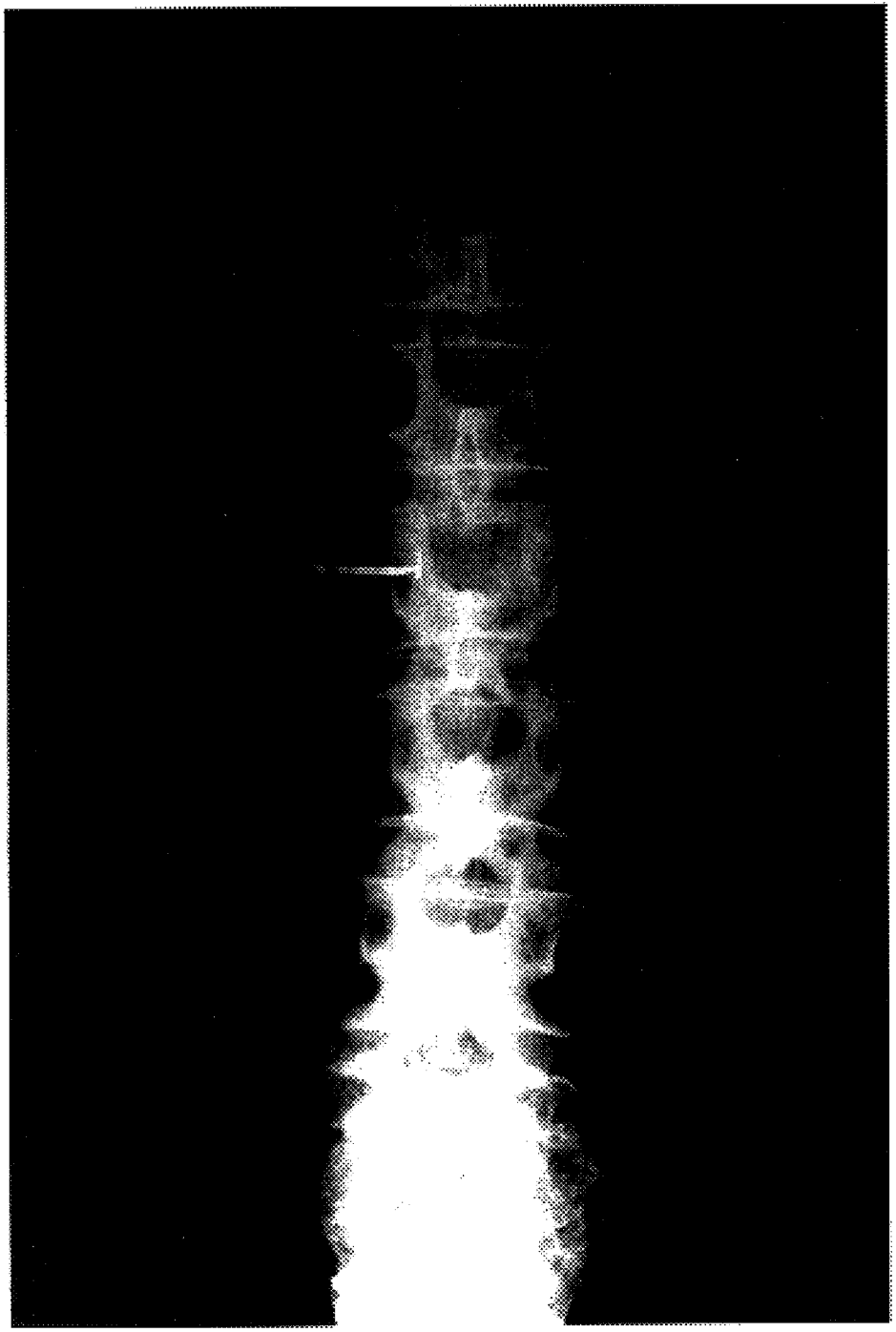
FIG. 20 is an X-ray photograph of a human cadaver osteoporotic spinal showing placement of needle prior to injection of PCA calcium phosphate.
Figure 21A:
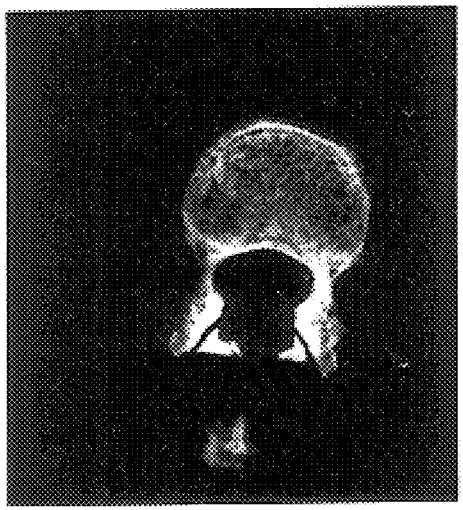
FIG. 21 is a photograph of the top view of an individual vertebra of a human cadaver before injection of the PCA calcium phosphate (FIG. 21a) and after injection (FIG. 21b).
Figure 21B:
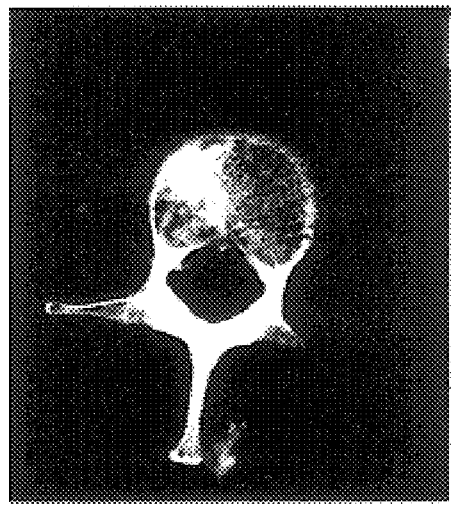

A spinal cord was obtained from the cadaver of an osteoporotic patient. Injectable PCA was prepared as Type 10 described in example 18 using 1.5 mls of water per gram PCA as a hydrating agent. A 16 gauge bone biopsy needle (a Quantico bone needle is also useful for this purpose) was inserted into the trabecular vertebral bone (FIG. 20). A second 16 gauge needle affixed to an empty 50 cc syringe was inserted into the opposite side of the same vertebrae. Needle location was confirmed by X-ray (FIG. 20). Following confirmation of needle location, a syringe containing freshly hydrated PCA was affixed to the bone biopsy needle. PCA calcium phosphate was slowly injected from syringe with the biopsy needle simultaneous with slowly withdrawing the needle and applying gentle suction through the 50 cc syringe. The injected PCA can be seen as an electron dense area within the vertebrae in the X-rays in FIG. 21$b$, as compared to the osteoporotic vertebrae before implantation (FIG. 21$a$). These results confirm the injectability of the inventive PCA calcium phosphate paste into the spinal cord of an osteoporotic patient.

EXAMPLE 25

Canine anterior lumbar interbody fusion. This example describes the use of PCA calcium phosphate in the fusion of canine spinal vertebrae.

Animals were anesthetized as described in Example 26, positioned in the right lateral decubitus position, shaved from anterior to posterior midline, extending form mid thorax to the pelvis. Following sterile prep and drape, a standard left retroperitoneal approach to the anterior lumbar spine was performed, with exposure of the L3–L6 vertebrae. The segmental vessels overlying L4 and L5 were ligated and divided, allowing anterolateral exposure of the L3–4, L4–5 and L5–6 discs. Anterior discectomies were performed at each level with the endplate prepared parallel and to bleeding subchondral bone using a parallel-paired-bladed oscillating saw (Aesculap). Following discectomy, a cylindrical titanium cage containing either PCA calcium phosphate or autologous bone or an unfilled cage was inserted into each disc space. Autogenous iliac crest bone graft was harvested from the left anterior iliac crest through a separate incision just prior to its packing into the cage and insertion into the disc space. After all three cages were inserted, internal fixation was applied using 4.5 mm vertebral body screws and a 6 mm diameter longitudinal rod from L3 to L6. Closure of the abdominal wound and iliac crest graft site was then done in layers using absorbable sutures and skin staples.

Dogs are sacrificed at two and twelve weeks and the histology of undecalcified sections are examined for evidence of new bone growth and vertebral fusion. Upon visual inspection on explant, the spinal cords using the PCA calcium phosphate of the invention appeared fused.

OTHER EMBODIMENTS

It will be understood that the foregoing is merely descriptive of certain preferred embodiments of the invention and is not intended to be limiting thereof. The following claims cover all of the generic and specific features of the invention herein described in the text and accompanying drawings.

What is claimed is:

1. A method of preparing a ceramic implant, comprising: mixing in any order,
   (a) a reactive amorphous calcium phosphate,
   (b) a second calcium phosphate, wherein the second calcium phosphate has a calcium to phosphate ratio of less than or equal to 1.67, and
   (c) a physiological liquid, said liquid in the amount to provide a paste or putty; and
   introducing the paste or putty into an implant site.

2. The method of claim 1, wherein the liquid is selected from the group consisting of water, a physiologically acceptable pH-buffered solution, saline solution, serum and tissue culture medium.

3. The method of claim 1, wherein the paste or putty is injected into the implant site.

4. The method of claim 1 wherein the second calcium phosphate is selected from the group consisting of calcium metaphosphate, dicalcium phosphate dihydrate, heptacalcium phosphate, tricalcium phosphate dihydrate, crystalline hydroxyapatite (HA), poorly crystalline calcium phosphate (PCA), calcium pyroposphate, monetite, otacalcium, phosphate, and amorphous calcium phosphate.

5. The method of claim 1 wherein the second calcium phosphate has a calcium to phosphate ratio of about 0.50 to 1.67.

6. The method of claim 1 wherein the paste or putty hardens at the implant site to form a poorly crystalline apatitic calcium phosphate.

7. The method of claim 1 further comprising a supplemental material, wherein the supplemental material is selected to impart a pre-selected characteristic to the implant.

8. The method of claim 7 wherein the supplemental material is selected from the group consisting of bioerodible polymers and non-erodible materials.

9. The method of claim 1 further comprising a biologically active agent.

10. The method of claim 9 wherein the biologically active agent is selected from the group consisting of bone morphogenetic proteins, antibiotics, polynucleotides, anti-cancer substances, growth factors, antigens and vaccines.

11. The method of claim 1 further comprising a cell.

12. The method of claim 11 wherein the cell is selected from the group consisting of osteoblasts, osteoclasts, chondrocytes, osteocytes, and fibroblasts.

13. An implant material comprising:
    (a) an amorphous calcium phosphate
    (b) a second calcium phosphate, wherein the second calcium phosphate has a calcium to phosphate ratio of less than or equal to 1.67; and
    (c) a physiological liquid, said liquid in the amount to provide a paste or putty.

14. The implant material of claim 13 therein the second calcium phosphate is selected from the group consisting of calcium metaphosphate, dicalcium phosphate dihydrate, heptacalcium phosphate, tricalcium phosphates, calcium pyrophosphate dihydrate, crystalline hydroxyapatite (HA), poorly crystalline calcium phosphate (PCA), calcium pyroposphate, monetite, otacalcium phosphate, and amorphous calcium phosphate.

15. The implant material of claim 13 wherein the second calcium phosphate has a calcium to phosphate ratio of 0.50 to 1.67.

16. The implant material of claim 13 wherein the paste converts into a poorly crystalline apatitic (PCA) calcium phosphate.

17. The implant material of claim 13 wherein the paste hardens in association with an endothermic reaction.

18. The implant material of claim 13 wherein the paste remains injectable or formable for a time greater than 60 minutes at room temperature.

19. The implant material of claim 13 wherein the paste hardens within 60 minutes in vivo.

20. The implant material of claim 13 wherein the paste remains injectable or formable at room temperature for a time greater than the time the paste hardens in vivo.

21. The implant material of claim 13 further comprising a biologically active agent.

22. The implant material of claim 21 wherein the biologically active agent is selected from the group consisting of bone morphogenetic proteins, antibiotics, polynucleotides, anti-cancer substances, growth factors, antigens and vaccines.

23. The implant material of claim 13 further comprising a supplemental material, wherein the supplemental material is selected to impart a pre-selected characteristic to the implant.

24. The implant material of claim 23 wherein the supplemental material is selected from the group consisting of bioerodible polymers and non-erodible materials.

25. The implant material of claim 13 further comprising a cell.

26. The implant material of claim 25 wherein the cell is selected from the group consisting of osteoblasts, osteoclasts, chondrocytes, osteocytes, and fibroblasts.

27. A kit, comprising:
    a powder mixture of an amorphous calcium phosphate and a second calcium phosphate, wherein the second calcium phosphate has a calcium to phosphate ratio of less than or equal to 1.67; and
    a mixing device for receipt of said powder mixture and a physiologically acceptable fluid.

* * * * *

UNITED STATES PATENT AND TRADEMARK OFFICE
CERTIFICATE OF CORRECTION

PATENT NO.   : 6,287,341 B1
DATED        : September 11, 2001
INVENTOR(S)  : Dosuk D. Lee et al.

It is certified that error appears in the above-identified patent and that said Letters Patent is hereby corrected as shown below:

<u>Column 33,</u>
Line 36, replace "a reactive amorphous calcium phosphate" with -- amorphous calcium phosphate --.
Line 52, replace "tricalcium phosphate dihydrate," with -- tricalcium phosphates, calcium pyrophosphate dihydrate, --.

Signed and Sealed this

Twenty-fourth Day of September, 2002

*Attest:*

*Attesting Officer*

JAMES E. ROGAN
*Director of the United States Patent and Trademark Office*